US006252135B1

(12) United States Patent
Chiang et al.

(10) Patent No.: US 6,252,135 B1
(45) Date of Patent: Jun. 26, 2001

(54) PRODUCTION OF SYRINGYL LIGNIN IN GYMNOSPERMS

(75) Inventors: Vincent L. Chiang, Hancock, MI (US); Daniel T. Carraway, Bainbridge, GA (US); Richard H. Smeltzer, Tallahassee, FL (US)

(73) Assignee: International Paper Company, Purchase, NY (US)

( * ) Notice: Subject to any disclaimer, the term of this patent is extended or adjusted under 35 U.S.C. 154(b) by 0 days.

(21) Appl. No.: 08/991,677

(22) Filed: Dec. 16, 1997

Related U.S. Application Data

(60) Provisional application No. 60/033,381, filed on Dec. 16, 1996.

(51) Int. Cl.[7] ............................. A01H 5/00; A01H 7/00; C12N 15/82; C12N 15/87; C12N 15/29
(52) U.S. Cl. .................... 800/278; 435/69.1; 435/468; 435/422; 435/419; 536/23.2; 536/23.6; 800/284; 800/319
(58) Field of Search ........................... 435/69.1, 468, 435/422, 419; 536/23.2, 23.6; 800/278, 284, 286, 287, 290, 292, 293, 294, 295, 319, 298

(56) References Cited

U.S. PATENT DOCUMENTS

| 4,795,855 | 1/1989 | Fillatti et al. ................ 800/288 |
| 4,801,545 | 1/1989 | Stuart et al. ................ 435/430.1 |
| 4,886,937 | 12/1989 | Sederoff et al. ................ 800/294 |
| 4,957,866 | 9/1990 | Gupta et al. ................ 435/422 |
| 5,034,322 | 7/1991 | Rogers et al. ................ 435/252.2 |
| 5,034,326 | 7/1991 | Pullman et al. ................ 435/422 |
| 5,107,065 | 4/1992 | Shewmaker et al. ................ 800/298 |
| 5,122,466 | 6/1992 | Stomp et al. ................ 800/293 |
| 5,187,092 * | 2/1993 | Uddin ................ 435/422 |
| 5,236,841 | 8/1993 | Gupta et al. ................ 435/422 |
| 5,294,549 | 3/1994 | Pullman et al. ................ 435/422 |
| 5,413,930 | 5/1995 | Becwar et al. ................ 435/422 |
| 5,451,514 * | 9/1995 | Boudet et al. ................ 800/286 |
| 5,457,041 | 10/1995 | Ginaven et al. ................ 435/455 |

OTHER PUBLICATIONS

"cDNA cloning, sequence analysis and seasonal expression of lignin–bispecific caffeic acid/5–hydroxyferulic acid O–methyltransferase of aspen", by Robert C. Bugos, et al, Plant Molecular Biology 17: 1203–1215, 1991.

"Genetic engineering of wood", by Ross Whetten, et al, Forest Ecology and Management, 43 (1991) 301–316, Elsevier Science Publishers B.V., Amsterdam.

"Logger and Lumberman" from Trailer Director Portable Sawmills & Firewood Processors, Dec. 15, 1995.

* cited by examiner

Primary Examiner—David T. Fox
Assistant Examiner—Ousama Zaghmout
(74) Attorney, Agent, or Firm—Luedeka, Neely & Graham, P.C.

(57) ABSTRACT

The present invention relates to a method for producing syringyl lignin in gymnosperms. The production of syringyl lignin in gymnosperms is accomplished by genetically transforming a gymnosperm genome, which does not normally contain genes which code for enzymes necessary for production of syringyl lignin, with DNA which codes for enzymes found in angiosperms associated with production of syringyl lignin. The expression of the inserted DNA is mediated using host promoter regions in the gymnosperm. In addition, genetic sequences which code for gymnosperm lignin anti-sense mRNA may be incorporated into the gymnosperm genome in order to suppress the formation of the less preferred forms of lignin in the gymnosperm such as guaiacyl lignin.

7 Claims, 33 Drawing Sheets

SEQ ID 5

```
<400> 5
cggcacgagc cctacctcct ttcttggaaa aatttcccca ttcgatcaca atccgggcct    60 caaaaa atg gga tca aca agc gaa acg aag atg agc ccg agt gaa gca      108
       Met Gly Ser Thr Ser Glu Thr Lys Met Ser Pro Ser Glu Ala
        1               5                  10 gca gca gca gaa gaa gaa gca ttc gta ttc gct atg caa tta acc agt    156
Ala Ala Ala Glu Glu Glu Ala Phe Val Phe Ala Met Gln Leu Thr Ser
 15              20                  25                  30 gct tca gtt ctt ccc atg gtc cta aaa tca gcc ata gag ctc gac gtc    204
Ala Ser Val Leu Pro Met Val Leu Lys Ser Ala Ile Glu Leu Asp Val
                 35                  40                  45 tta gaa atc atg gct aaa gct ggt cca ggt gcg cac ata tcc aca tct    252
Leu Glu Ile Met Ala Lys Ala Gly Pro Gly Ala His Ile Ser Thr Ser
             50                  55                  60 gac ata gcc tct aag ctg ccc aca aag aat cca gat gca gcc gtc atg    300
Asp Ile Ala Ser Lys Leu Pro Thr Lys Asn Pro Asp Ala Ala Val Met
         65                  70                  75 ctt gac cgt atg ctc cgc ctc ttg gct agc tac tct gtt cta acg tgc    348
Leu Asp Arg Met Leu Arg Leu Leu Ala Ser Tyr Ser Val Leu Thr Cys
     80                  85                  90 tct ctc cgc acc ctc cct gac ggc aag atc gag agg ctt tac ggc ctt    396
Ser Leu Arg Thr Leu Pro Asp Gly Lys Ile Glu Arg Leu Tyr Gly Leu
 95                 100                 105                 110 gca ccc gtt tgt aaa ttc ttg acc aga aac gat gat gga gtc tcc ata    444
Ala Pro Val Cys Lys Phe Leu Thr Arg Asn Asp Asp Gly Val Ser Ile
                115                 120                 125 gcc gct ctg tct ctc atg aat caa gac aag gtc ctc atg gag agc tgg    492
Ala Ala Leu Ser Leu Met Asn Gln Asp Lys Val Leu Met Glu Ser Trp
            130                 135                 140 tac cac ttg acc gag gca gtt ctt gaa ggt gga att cca ttt aac aag    540
Tyr His Leu Thr Glu Ala Val Leu Glu Gly Gly Ile Pro Phe Asn Lys
        145                 150                 155
```

Fig. 2A

SEQ ID 5

| | |
|---|---|
| gcc tat gga atg aca gca ttt gag tac cat ggc acc gat ccc aga ttc<br>Ala Tyr Gly Met Thr Ala Phe Glu Tyr His Gly Thr Asp Pro Arg Phe<br>160 165 170 | 588 |
| aac aca gtt ttc aac aat gga atg tcc aat cat tcg acc att acc atg<br>Asn Thr Val Phe Asn Asn Gly Met Ser Asn His Ser Thr Ile Thr Met<br>175 180 185 190 | 636 |
| aag aaa atc ctt gag act tac aaa ggg ttc gag gga ctt gga tct gtg<br>Lys Lys Ile Leu Glu Thr Tyr Lys Gly Phe Glu Gly Leu Gly Ser Val<br>195 200 205 | 684 |
| gtt gat gtt ggt ggt ggc act ggt gcc cac ctt aac atg att atc gct<br>Val Asp Val Gly Gly Gly Thr Gly Ala His Leu Asn Met Ile Ile Ala<br>210 215 220 | 732 |
| aaa tac ccc atg atc aag ggc att aac ttc gac ttg cct cat gtt att<br>Lys Tyr Pro Met Ile Lys Gly Ile Asn Phe Asp Leu Pro His Val Ile<br>225 230 235 | 780 |
| gag gag gct ccc tcc tat cct ggt gtg gag cat gtt ggt gga gat atg<br>Glu Glu Ala Pro Ser Tyr Pro Gly Val Glu His Val Gly Gly Asp Met<br>240 245 250 | 828 |
| ttt gtt agt gtt cca aaa gga gat gcc att ttc atg aag tgg ata tgt<br>Phe Val Ser Val Pro Lys Gly Asp Ala Ile Phe Met Lys Trp Ile Cys<br>255 260 265 270 | 876 |
| cat gat tgg agc gat gaa cac tgc ttg aag ttt ttg aag aaa tgt tat<br>His Asp Trp Ser Asp Glu His Cys Leu Lys Phe Leu Lys Lys Cys Tyr<br>275 280 285 | 924 |
| gaa gca ctt cca acc aat ggg aag gtg atc ctt gct gaa tgc atc ctc<br>Glu Ala Leu Pro Thr Asn Gly Lys Val Ile Leu Ala Glu Cys Ile Leu<br>290 295 300 | 972 |
| ccc gtg gcg cca gac gca agc ctc ccc act aag gca gtg gtc cat att<br>Pro Val Ala Pro Asp Ala Ser Leu Pro Thr Lys Ala Val Val His Ile<br>305 310 315 | 1020 |
| gat gtc atc atg ttg gct cat aac cca ggt ggg aaa gag aga act gag<br>Asp Val Ile Met Leu Ala His Asn Pro Gly Gly Lys Glu Arg Thr Glu<br>320 325 330 | 1068 |
| aag gag ttt gag gcc ttg gcc aag ggg gct gga ttt gaa ggt ttc cga<br>Lys Glu Phe Glu Ala Leu Ala Lys Gly Ala Gly Phe Glu Gly Phe Arg | 1116 |

Fig. 2B

SEQ ID 5

```
         335              340              345              350
gta gta gcc tcg tgc gct tac aat aca tgg atc atc gaa ttt ttg aag    1164
Val Val Ala Ser Cys Ala Tyr Asn Thr Trp Ile Ile Glu Phe Leu Lys
                355              360              365 aag att tgagtcctta ctcggctttg agtacataat accaactcct tttggttttc    1220
Lys Ile gagattgtga ttgtgattgt gattgtctct ctttcgcagt tggccttatg atataatgta 1280
tcgttaactc gatcacagaa gtgcaaaaga cagtgaatgt acactgcttt ataaaataaa 1340
aattttaaga ttttgattca tgtaaaaaaa aaaaaaaaa                        1380
```

Fig. 2C

SEQ ID 6

<400> 6

| | | | | | | | | | | | | | | |
|---|---|---|---|---|---|---|---|---|---|---|---|---|---|---|
| Met | Gly | Ser | Thr | Ser | Glu | Thr | Lys | Met | Ser | Pro | Ser | Glu | Ala | Ala | Ala |
| 1 | | | | 5 | | | | | 10 | | | | | 15 | |

Ala Glu Glu Glu Ala Phe Val Phe Ala Met Gln Leu Thr Ser Ala Ser
            20                  25                  30

Val Leu Pro Met Val Leu Lys Ser Ala Ile Glu Leu Asp Val Leu Glu
        35                  40                  45

Ile Met Ala Lys Ala Gly Pro Gly Ala His Ile Ser Thr Ser Asp Ile
    50                  55                  60

Ala Ser Lys Leu Pro Thr Lys Asn Pro Asp Ala Ala Val Met Leu Asp
65                  70                  75                  80

Arg Met Leu Arg Leu Leu Ala Ser Tyr Ser Val Leu Thr Cys Ser Leu
            85                  90                  95

Arg Thr Leu Pro Asp Gly Lys Ile Glu Arg Leu Tyr Gly Leu Ala Pro
            100                 105                 110

Val Cys Lys Phe Leu Thr Arg Asn Asp Asp Gly Val Ser Ile Ala Ala
            115                 120                 125

Leu Ser Leu Met Asn Gln Asp Lys Val Leu Met Glu Ser Trp Tyr His
130                 135                 140

Leu Thr Glu Ala Val Leu Glu Gly Gly Ile Pro Phe Asn Lys Ala Tyr
145                 150                 155                 160

Gly Met Thr Ala Phe Glu Tyr His Gly Thr Asp Pro Arg Phe Asn Thr
                165                 170                 175

Val Phe Asn Asn Gly Met Ser Asn His Ser Thr Ile Thr Met Lys Lys
            180                 185                 190

Ile Leu Glu Thr Tyr Lys Gly Phe Glu Gly Leu Gly Ser Val Val Asp
            195                 200                 205

Val Gly Gly Gly Thr Gly Ala His Leu Asn Met Ile Ile Ala Lys Tyr
210                 215                 220

Pro Met Ile Lys Gly Ile Asn Phe Asp Leu Pro His Val Ile Glu Glu
225                 230                 235                 240

Fig. 2D

SEQ ID 6

Ala Pro Ser Tyr Pro Gly Val Glu His Val Gly Gly Asp Met Phe Val
                245                 250                 255

Ser Val Pro Lys Gly Asp Ala Ile Phe Met Lys Trp Ile Cys His Asp
            260                 265                 270

Trp Ser Asp Glu His Cys Leu Lys Phe Leu Lys Lys Cys Tyr Glu Ala
        275                 280                 285

Leu Pro Thr Asn Gly Lys Val Ile Leu Ala Glu Cys Ile Leu Pro Val
    290                 295                 300

Ala Pro Asp Ala Ser Leu Pro Thr Lys Ala Val Val His Ile Asp Val
305                 310                 315                 320

Ile Met Leu Ala His Asn Pro Gly Gly Lys Glu Arg Thr Glu Lys Glu
                325                 330                 335

Phe Glu Ala Leu Ala Lys Gly Ala Gly Phe Glu Gly Phe Arg Val Val
            340                 345                 350

Ala Ser Cys Ala Tyr Asn Thr Trp Ile Ile Glu Phe Leu Lys Lys Ile
        355                 360                 365

Fig. 2E

SEQ ID 7

```
<400> 7
cggcacgagc tcattttcca cttctggttt gatctctgca attcttccat cagtccta    59 atg gag acc caa aca aaa caa gaa gaa atc ata tat cgg tcg aaa ctc   107
Met Glu Thr Gln Thr Lys Gln Glu Glu Ile Ile Tyr Arg Ser Lys Leu
  1               5                  10                  15 ccc gat atc tac atc ccc aaa cac ctc cct tta cat tcg tat tgt ttc   155
Pro Asp Ile Tyr Ile Pro Lys His Leu Pro Leu His Ser Tyr Cys Phe
             20                  25                  30 gag aac atc tca cag ttc ggc tcc cgc ccc tgt ctg atc aat ggc gca   203
Glu Asn Ile Ser Gln Phe Gly Ser Arg Pro Cys Leu Ile Asn Gly Ala
         35                  40                  45 acg ggc aag tat tac aca tat gct gag gtt gag ctc att gcg cgc aag   251
Thr Gly Lys Tyr Tyr Thr Tyr Ala Glu Val Glu Leu Ile Ala Arg Lys
     50                  55                  60 gtc gca tcc ggc ctc aac aaa ctc ggc gtt cga caa ggt gac atc atc   299
Val Ala Ser Gly Leu Asn Lys Leu Gly Val Arg Gln Gly Asp Ile Ile
 65                  70                  75                  80 atg ctt ttg cta ccc aac tcg ccg gag ttc gtg ttt tca att ctc ggc   347
Met Leu Leu Leu Pro Asn Ser Pro Glu Phe Val Phe Ser Ile Leu Gly
                 85                  90                  95 gca tcc tac cgc ggg gct gcc gcc acc gcc gca aac ccg ttt tat acc   395
Ala Ser Tyr Arg Gly Ala Ala Ala Thr Ala Ala Asn Pro Phe Tyr Thr
            100                 105                 110 cct gcc gag atc agg aag caa gcc aaa acc tcc aac gcc agg ctt att   443
Pro Ala Glu Ile Arg Lys Gln Ala Lys Thr Ser Asn Ala Arg Leu Ile
        115                 120                 125 atc aca cat gcc tgt tac tat gag aaa gtg aag gac ttg gtg gaa gag   491
Ile Thr His Ala Cys Tyr Tyr Glu Lys Val Lys Asp Leu Val Glu Glu
    130                 135                 140 aac gtt gcc aag atc ata tgt ata gac tca ccc ccg gac ggt tgt ttg   539
Asn Val Ala Lys Ile Ile Cys Ile Asp Ser Pro Pro Asp Gly Cys Leu
145                 150                 155                 160
```

Fig. 3A

SEQ ID 7

| | | | | | | | | | | | | | | | |
|---|---|---|---|---|---|---|---|---|---|---|---|---|---|---|---|
| cac | ttc | tcg | g..g | ctg | agt | gag | gcg | gac | gag | aac | gac | atg | ccc | aat | gta | 587 |
| His | Phe | Ser | Glu | Leu | Ser | Glu | Ala | Asp | Glu | Asn | Asp | Met | Pro | Asn | Val |
| | | | | 165 | | | | | 170 | | | | | 175 | | gag att gac ccc gat gat gtg gtg gcg ctg ccg tac tcg tca ggg acg    635
Glu Ile Asp Pro Asp Asp Val Val Ala Leu Pro Tyr Ser Ser Gly Thr
           180               185               190 acg ggt tta cca aag ggg gtg atg cta aca cac aag gga caa gtg acg    683
Thr Gly Leu Pro Lys Gly Val Met Leu Thr His Lys Gly Gln Val Thr
          195               200               205 agt gtg gcg caa cag gtg gac gga gag aat ccg aac ctg tat ata cat    731
Ser Val Ala Gln Gln Val Asp Gly Glu Asn Pro Asn Leu Tyr Ile His
210                    215               220 agc gag gac gtg gtt ctg tgc gtg ttg cct ctg ttt cac atc tac tcg    779
Ser Glu Asp Val Val Leu Cys Val Leu Pro Leu Phe His Ile Tyr Ser
225                    230             235            240 atg aac gtc atg ttt tgc ggg tta cga gtt ggt gcg gcg att ctg att    827
Met Asn Val Met Phe Cys Gly Leu Arg Val Gly Ala Ala Ile Leu Ile
               245              250             255 atg cag aaa ttt gaa ata tat ggg ttg tta gag ctg gtc aga agt aca    875
Met Gln Lys Phe Glu Ile Tyr Gly Leu Leu Glu Leu Val Arg Ser Thr
          260               265              270 ggt gac cat cat gcc tat cgt aca ccc atc gta ttg gca atc tcc aag    923
Gly Asp His His Ala Tyr Arg Thr Pro Ile Val Leu Ala Ile Ser Lys
          275               280              285 act ccg gat ctt cac aac tat gat gtg tcc tcc att cgg act gtc atg    971
Thr Pro Asp Leu His Asn Tyr Asp Val Ser Ser Ile Arg Thr Val Met
          290               295              300 tca ggt gcg gct cct ctg ggc aag gaa ctt gaa gat tct gtc aga gct    1019
Ser Gly Ala Ala Pro Leu Gly Lys Glu Leu Glu Asp Ser Val Arg Ala
305                    310             315            320 aag ttt ccc acc gcc aaa ctt ggt cag gga tat gga atg acg gag gca    1067
Lys Phe Pro Thr Ala Lys Leu Gly Gln Gly Tyr Gly Met Thr Glu Ala
               325              330             335 ggg ccc gtg cta gcg atg tgt ttg gca ttt gcc aag gaa ggg ttt gaa    1115
Gly Pro Val Leu Ala Met Cys Leu Ala Phe Ala Lys Glu Gly Phe Glu
               340              345             350

Fig. 3B

SEQ ID 7

```
ata aaa tcg ggg gca tct gga act gtt tta agg aac gca cag atg aag      1163
Ile Lys Ser Gly Ala Ser Gly Thr Val Leu Arg Asn Ala Gln Met Lys
        355             360                 365 att gtg gac cct gaa acc ggt gtc act ctc cct cga aac caa ccc gga      1211
Ile Val Asp Pro Glu Thr Gly Val Thr Leu Pro Arg Asn Gln Pro Gly
        370             375                 380 gag att tgc att aga gga gac caa atc atg aaa ggt tat ctt aat gat      1259
Glu Ile Cys Ile Arg Gly Asp Gln Ile Met Lys Gly Tyr Leu Asn Asp
385             390                 395                 400 cct gag gcg acg gag aga acc ata gac aag gaa ggt tgg tta cac aca      1307
Pro Glu Ala Thr Glu Arg Thr Ile Asp Lys Glu Gly Trp Leu His Thr
                405                 410                 415 ggt gat gtg ggc tac atc gac gat gac act gag ctc ttc att gtt gat      1355
Gly Asp Val Gly Tyr Ile Asp Asp Asp Thr Glu Leu Phe Ile Val Asp
                420                 425                 430 cgg ttg aag gaa ctg atc aaa tac aaa ggg ttt cag gtg gca ccc gct      1403
Arg Leu Lys Glu Leu Ile Lys Tyr Lys Gly Phe Gln Val Ala Pro Ala
        435                 440                 445 gag ctt gag gcc atg ctc ctc aac cat ccc aac atc tct gat gct gcc      1451
Glu Leu Glu Ala Met Leu Leu Asn His Pro Asn Ile Ser Asp Ala Ala
        450                 455                 460 gtc gtc cca atg aaa gac gat gaa gct gga gag ctc cct gtg gcg ttt      1499
Val Val Pro Met Lys Asp Asp Glu Ala Gly Glu Leu Pro Val Ala Phe
465             470                 475                 480 gtt gta aga tca gat ggt tct cag ata tcc gag gct gaa atc agg caa      1547
Val Val Arg Ser Asp Gly Ser Gln Ile Ser Glu Ala Glu Ile Arg Gln
                485                 490                 495 tac atc gca aaa cag gtg gtt ttt tat aaa aga ata cat cgc gta ttt      1595
Tyr Ile Ala Lys Gln Val Val Phe Tyr Lys Arg Ile His Arg Val Phe
                500                 505                 510 ttc gtc gaa gcc att cct aaa gcg ccc tct ggc aaa atc ttg cgg aag      1643
Phe Val Glu Ala Ile Pro Lys Ala Pro Ser Gly Lys Ile Leu Arg Lys
        515                 520                 525 gac ctg aga gcc aaa ttg gcg tct ggt ctt ccc aat taattctcat          1689
Asp Leu Arg Ala Lys Leu Ala Ser Gly Leu Pro Asn
        530                 535             540
```

Fig. 3C

SEQ ID 7

```
tcgctaccct cctttctctt atcatacgcc aacacgaacg aagaggctca attaaacgct 1749 gctcattcga agcggctcaa ttaaagctgc tcattcatgt ccaccgagtg ggcagcctgt 1809 cttgttggga tgttctttca tttgattcag ctgtgagaag ccagaccctc attatttatt 1869 gtgaaattca caagaatgtc tgtaaatcga tgttgtgagt gatgggtttc aaaacacttt 1929 tgacattgtt tacgttgtat ttcctgctgt tgaaaataac tactttgtat gacttttatt 1989 tgggaagata acctttcaaa aaaaaaaaaa aaaaaa                             2025
```

Fig. 3D

SEQ ID 8

<400> 8

| Met | Glu | Thr | Gln | Thr | Lys | Gln | Glu | Ile | Ile | Tyr | Arg | Ser | Lys | Leu |
|---|---|---|---|---|---|---|---|---|---|---|---|---|---|---|
| 1 | | | | 5 | | | | | 10 | | | | | 15 |

| Pro | Asp | Ile | Tyr | Ile | Pro | Lys | His | Leu | Pro | Leu | His | Ser | Tyr | Cys | Phe |
|---|---|---|---|---|---|---|---|---|---|---|---|---|---|---|---|
| | | | 20 | | | | | 25 | | | | | 30 | | |

| Glu | Asn | Ile | Ser | Gln | Phe | Gly | Ser | Arg | Pro | Cys | Leu | Ile | Asn | Gly | Ala |
|---|---|---|---|---|---|---|---|---|---|---|---|---|---|---|---|
| | | | 35 | | | | | 40 | | | | | 45 | | |

| Thr | Gly | Lys | Tyr | Tyr | Thr | Tyr | Ala | Glu | Val | Glu | Leu | Ile | Ala | Arg | Lys |
|---|---|---|---|---|---|---|---|---|---|---|---|---|---|---|---|
| | 50 | | | | | 55 | | | | | 60 | | | | |

| Val | Ala | Ser | Gly | Leu | Asn | Lys | Leu | Gly | Val | Arg | Gln | Gly | Asp | Ile | Ile |
|---|---|---|---|---|---|---|---|---|---|---|---|---|---|---|---|
| 65 | | | | | 70 | | | | | 75 | | | | | 80 |

| Met | Leu | Leu | Leu | Pro | Asn | Ser | Pro | Glu | Phe | Val | Phe | Ser | Ile | Leu | Gly |
|---|---|---|---|---|---|---|---|---|---|---|---|---|---|---|---|
| | | | | 85 | | | | | 90 | | | | | 95 | |

| Ala | Ser | Tyr | Arg | Gly | Ala | Ala | Ala | Thr | Ala | Ala | Asn | Pro | Phe | Tyr | Thr |
|---|---|---|---|---|---|---|---|---|---|---|---|---|---|---|---|
| | | | 100 | | | | | 105 | | | | | 110 | | |

| Pro | Ala | Glu | Ile | Arg | Lys | Gln | Ala | Lys | Thr | Ser | Asn | Ala | Arg | Leu | Ile |
|---|---|---|---|---|---|---|---|---|---|---|---|---|---|---|---|
| | | | 115 | | | | | 120 | | | | | 125 | | |

| Ile | Thr | His | Ala | Cys | Tyr | Tyr | Glu | Lys | Val | Lys | Asp | Leu | Val | Glu | Glu |
|---|---|---|---|---|---|---|---|---|---|---|---|---|---|---|---|
| | 130 | | | | | 135 | | | | | 140 | | | | |

| Asn | Val | Ala | Lys | Ile | Ile | Cys | Ile | Asp | Ser | Pro | Pro | Asp | Gly | Cys | Leu |
|---|---|---|---|---|---|---|---|---|---|---|---|---|---|---|---|
| 145 | | | | | 150 | | | | | 155 | | | | | 160 |

| His | Phe | Ser | Glu | Leu | Ser | Glu | Ala | Asp | Glu | Asn | Asp | Met | Pro | Asn | Val |
|---|---|---|---|---|---|---|---|---|---|---|---|---|---|---|---|
| | | | | 165 | | | | | 170 | | | | | 175 | |

| Glu | Ile | Asp | Pro | Asp | Asp | Val | Val | Ala | Leu | Pro | Tyr | Ser | Ser | Gly | Thr |
|---|---|---|---|---|---|---|---|---|---|---|---|---|---|---|---|
| | | | 180 | | | | | 185 | | | | | 190 | | |

| Thr | Gly | Leu | Pro | Lys | Gly | Val | Met | Leu | Thr | His | Lys | Gly | Gln | Val | Thr |
|---|---|---|---|---|---|---|---|---|---|---|---|---|---|---|---|
| | | | 195 | | | | | 200 | | | | | 205 | | |

| Ser | Val | Ala | Gln | Gln | Val | Asp | Gly | Glu | Asn | Pro | Asn | Leu | Tyr | Ile | His |
|---|---|---|---|---|---|---|---|---|---|---|---|---|---|---|---|
| | 210 | | | | | 215 | | | | | 220 | | | | |

| Ser | Glu | Asp | Val | Val | Leu | Cys | Val | Leu | Pro | Leu | Phe | His | Ile | Tyr | Ser |
|---|---|---|---|---|---|---|---|---|---|---|---|---|---|---|---|
| 225 | | | | | 230 | | | | | 235 | | | | | 240 |

Fig. 3E

SEQ ID 8

Met Asn Val Met Phe Cys Gly Leu Arg Val Gly Ala Ala Ile Leu Ile
            245                 250                 255

Met Gln Lys Phe Glu Ile Tyr Gly Leu Leu Glu Leu Val Arg Ser Thr
            260                 265                 270

Gly Asp His His Ala Tyr Arg Thr Pro Ile Val Leu Ala Ile Ser Lys
            275                 280                 285

Thr Pro Asp Leu His Asn Tyr Asp Val Ser Ser Ile Arg Thr Val Met
            290                 295                 300

Ser Gly Ala Ala Pro Leu Gly Lys Glu Leu Glu Asp Ser Val Arg Ala
305                 310                 315                 320

Lys Phe Pro Thr Ala Lys Leu Gly Gln Gly Tyr Gly Met Thr Glu Ala
            325                 330                 335

Gly Pro Val Leu Ala Met Cys Leu Ala Phe Ala Lys Glu Gly Phe Glu
            340                 345                 350

Ile Lys Ser Gly Ala Ser Gly Thr Val Leu Arg Asn Ala Gln Met Lys
            355                 360                 365

Ile Val Asp Pro Glu Thr Gly Val Thr Leu Pro Arg Asn Gln Pro Gly
            370                 375                 380

Glu Ile Cys Ile Arg Gly Asp Gln Ile Met Lys Gly Tyr Leu Asn Asp
385                 390                 395                 400

Pro Glu Ala Thr Glu Arg Thr Ile Asp Lys Glu Gly Trp Leu His Thr
            405                 410                 415

Gly Asp Val Gly Tyr Ile Asp Asp Thr Glu Leu Phe Ile Val Asp
            420                 425                 430

Arg Leu Lys Glu Leu Ile Lys Tyr Lys Gly Phe Gln Val Ala Pro Ala
            435                 440                 445

Glu Leu Glu Ala Met Leu Leu Asn His Pro Asn Ile Ser Asp Ala Ala
            450                 455                 460

Val Val Pro Met Lys Asp Asp Glu Ala Gly Glu Leu Pro Val Ala Phe
465                 470                 475                 480

Fig. 3F

SEQ ID 8

Val Val Arg Ser Asp Gly Ser Gln Ile Ser Glu Ala Glu Ile Arg Gln
                485             490                 495

Tyr Ile Ala Lys Gln Val Val Phe Tyr Lys Arg Ile His Arg Val Phe
            500             505                 510

Phe Val Glu Ala Ile Pro Lys Ala Pro Ser Gly Lys Ile Leu Arg Lys
        515             520                 525

Asp Leu Arg Ala Lys Leu Ala Ser Gly Leu Pro Asn
    530             535             540

Fig. 3G

SEQ ID 1

| | | | | | | | | | | | | | | | | |
|---|---|---|---|---|---|---|---|---|---|---|---|---|---|---|---|---|
| cggcacgagg | aaaccctaaa | actcacctct | cttacccttt | ctcttca | atg | gct | ttc | | | | | | | | | 56 |
| | | | | | Met | Ala | Phe | | | | | | | | | |
| | | | | | 1 | | | | | | | | | | | |

| ctt | cta | ata | ccc | atc | tca | ata | atc | ttc | atc | gtc | tta | gct | tac | cag | ctc | 104 |
|---|---|---|---|---|---|---|---|---|---|---|---|---|---|---|---|---|
| Leu | Leu | Ile | Pro | Ile | Ser | Ile | Ile | Phe | Ile | Val | Leu | Ala | Tyr | Gln | Leu | |
| | | 5 | | | | 10 | | | | | 15 | | | | | |

| tat | caa | cgg | ctc | aga | ttt | aag | ctc | cca | ccc | ggc | cca | cgt | cca | tgg | ccg | 152 |
|---|---|---|---|---|---|---|---|---|---|---|---|---|---|---|---|---|
| Tyr | Gln | Arg | Leu | Arg | Phe | Lys | Leu | Pro | Pro | Gly | Pro | Arg | Pro | Trp | Pro | |
| 20 | | | | | 25 | | | | | 30 | | | | | 35 | |

| atc | gtc | gga | aac | ctt | tac | gac | ata | aaa | ccg | gtg | agg | ttc | cgg | tgt | ttc | 200 |
|---|---|---|---|---|---|---|---|---|---|---|---|---|---|---|---|---|
| Ile | Val | Gly | Asn | Leu | Tyr | Asp | Ile | Lys | Pro | Val | Arg | Phe | Arg | Cys | Phe | |
| | | | | 40 | | | | | 45 | | | | | 50 | | |

| gcc | gag | tgg | tca | caa | gcg | tac | ggt | ccg | atc | ata | tcg | gtg | tgg | ttc | ggt | 248 |
|---|---|---|---|---|---|---|---|---|---|---|---|---|---|---|---|---|
| Ala | Glu | Trp | Ser | Gln | Ala | Tyr | Gly | Pro | Ile | Ile | Ser | Val | Trp | Phe | Gly | |
| | | | 55 | | | | 60 | | | | | 65 | | | | |

| tca | acg | ttg | aat | gtg | atc | gta | tcg | aat | tcg | gaa | ttg | gct | aag | gaa | gtg | 296 |
|---|---|---|---|---|---|---|---|---|---|---|---|---|---|---|---|---|
| Ser | Thr | Leu | Asn | Val | Ile | Val | Ser | Asn | Ser | Glu | Leu | Ala | Lys | Glu | Val | |
| | | 70 | | | | 75 | | | | | 80 | | | | | |

| ctc | aag | gaa | aaa | gat | caa | caa | ttg | gct | gat | agg | cat | agg | agt | aga | tca | 344 |
|---|---|---|---|---|---|---|---|---|---|---|---|---|---|---|---|---|
| Leu | Lys | Glu | Lys | Asp | Gln | Gln | Leu | Ala | Asp | Arg | His | Arg | Ser | Arg | Ser | |
| | 85 | | | | | 90 | | | | | 95 | | | | | |

| gct | gcc | aaa | ttt | agc | agg | gat | ggg | cag | gac | ctt | ata | tgg | gct | gat | tat | 392 |
|---|---|---|---|---|---|---|---|---|---|---|---|---|---|---|---|---|
| Ala | Ala | Lys | Phe | Ser | Arg | Asp | Gly | Gln | Asp | Leu | Ile | Trp | Ala | Asp | Tyr | |
| 100 | | | | | 105 | | | | | 110 | | | | | 115 | |

| gga | cct | cac | tat | gtg | aag | gtt | aca | aag | gtt | tgt | acc | ctc | gag | ctt | ttt | 440 |
|---|---|---|---|---|---|---|---|---|---|---|---|---|---|---|---|---|
| Gly | Pro | His | Tyr | Val | Lys | Val | Thr | Lys | Val | Cys | Thr | Leu | Glu | Leu | Phe | |
| | | | 120 | | | | 125 | | | | | 130 | | | | |

| act | cca | aag | cgg | ctt | gaa | gct | ctt | aga | ccc | att | aga | gaa | gat | gaa | gtt | 488 |
|---|---|---|---|---|---|---|---|---|---|---|---|---|---|---|---|---|
| Thr | Pro | Lys | Arg | Leu | Glu | Ala | Leu | Arg | Pro | Ile | Arg | Glu | Asp | Glu | Val | |
| | | 135 | | | | | 140 | | | | | 145 | | | | |

| aca | gcc | atg | gtt | gag | tcc | att | ttt | aat | gac | act | gcg | aat | cct | gaa | aat | 536 |
|---|---|---|---|---|---|---|---|---|---|---|---|---|---|---|---|---|
| Thr | Ala | Met | Val | Glu | Ser | Ile | Phe | Asn | Asp | Thr | Ala | Asn | Pro | Glu | Asn | |
| | | 150 | | | | 155 | | | | | 160 | | | | | |

Fig. 4A

SEQ ID 1

| | | | | | | | | | | | | | | | |
|---|---|---|---|---|---|---|---|---|---|---|---|---|---|---|---|
| tat | ggg | aag | agt | atg | ctg | gtg | aag | aag | tat | ttg | gga | gca | gta | gca | ttc | 584 |
| Tyr | Gly | Lys | Ser | Met | Leu | Val | Lys | Lys | Tyr | Leu | Gly | Ala | Val | Ala | Phe |
| | 165 | | | | 170 | | | | | 175 | | | | | | aac aac att aca aga ctc gca ttt gga aag cga ttc gtg aat tca gag    632
Asn Asn Ile Thr Arg Leu Ala Phe Gly Lys Arg Phe Val Asn Ser Glu
180             185                 190                 195 ggt gta atg gac gag caa gga ctt gaa ttt aag gaa att gtg gcc aat    680
Gly Val Met Asp Glu Gln Gly Leu Glu Phe Lys Glu Ile Val Ala Asn
                200                 205                 210 gga ctc aag ctt ggt gcc tca ctt gca atg gct gag cac att cct tgg   728
Gly Leu Lys Leu Gly Ala Ser Leu Ala Met Ala Glu His Ile Pro Trp
            215                 220                 225 ctc cgt tgg atg ttc cca ctt gag gaa ggg gcc ttt gcc aag cat ggg   776
Leu Arg Trp Met Phe Pro Leu Glu Glu Gly Ala Phe Ala Lys His Gly
            230                 235                 240 gca cgt agg gac cga ctt acc aga gct atc atg gaa gag cac aca ata   824
Ala Arg Arg Asp Arg Leu Thr Arg Ala Ile Met Glu Glu His Thr Ile
    245                 250                 255 gcc cgt aaa aag agt ggt gga gcc caa caa cat ttc gtg gat gca ttg   872
Ala Arg Lys Lys Ser Gly Gly Ala Gln Gln His Phe Val Asp Ala Leu
260             265                 270                 275 ctc acc cta caa gag aaa tat gac ctt agc gag gac act att att ggg   920
Leu Thr Leu Gln Glu Lys Tyr Asp Leu Ser Glu Asp Thr Ile Ile Gly
            280                 285                 290 ctc ctt tgg gat atg atc act gca ggc atg gac aca acc gca atc tct   968
Leu Leu Trp Asp Met Ile Thr Ala Gly Met Asp Thr Thr Ala Ile Ser
            295                 300                 305 gtc gaa tgg gcc atg gcc gag tta att aag aac cca agg gtg caa caa   1016
Val Glu Trp Ala Met Ala Glu Leu Ile Lys Asn Pro Arg Val Gln Gln
            310                 315                 320 aaa gct caa gag gag cta gac aat gta ctt ggg tcc gaa cgt gtc ctg   1064
Lys Ala Gln Glu Glu Leu Asp Asn Val Leu Gly Ser Glu Arg Val Leu
325             330                 335

Fig. 4B

SEQ ID 1

| | | | | | | | | | | | | | | | |
|---|---|---|---|---|---|---|---|---|---|---|---|---|---|---|---|
| acc | gaa | ttg | gac | ttc | tca | agc | ctc | cct | tat | cta | caa | tgt | gta | gcc | aag | 1112 |
| Thr | Glu | Leu | Asp | Phe | Ser | Ser | Leu | Pro | Tyr | Leu | Gln | Cys | Val | Ala | Lys |
| 340 | | | | | 345 | | | | | 350 | | | | | 355 |

| | | | | | | | | | | | | | | | |
|---|---|---|---|---|---|---|---|---|---|---|---|---|---|---|---|
| gag | gca | cta | agg | ctg | cac | cct | cca | aca | cca | cta | atg | ctc | cct | cat | cgc | 1160 |
| Glu | Ala | Leu | Arg | Leu | His | Pro | Pro | Thr | Pro | Leu | Met | Leu | Pro | His | Arg |
| | | | | | 360 | | | | | 365 | | | | | 370 |

| | | | | | | | | | | | | | | | |
|---|---|---|---|---|---|---|---|---|---|---|---|---|---|---|---|
| gcc | aat | gcc | aac | gtc | aaa | att | ggt | ggc | tac | gac | atc | cct | aag | gga | tca | 1208 |
| Ala | Asn | Ala | Asn | Val | Lys | Ile | Gly | Gly | Tyr | Asp | Ile | Pro | Lys | Gly | Ser |
| | | | 375 | | | | | 380 | | | | | 385 | | |

| | | | | | | | | | | | | | | | |
|---|---|---|---|---|---|---|---|---|---|---|---|---|---|---|---|
| aat | gtt | cat | gta | aat | gtc | tgg | gcc | gtg | gct | cgt | gat | cca | gca | gtg | tgg | 1256 |
| Asn | Val | His | Val | Asn | Val | Trp | Ala | Val | Ala | Arg | Asp | Pro | Ala | Val | Trp |
| | | | 390 | | | | | 395 | | | | | 400 | | |

| | | | | | | | | | | | | | | | |
|---|---|---|---|---|---|---|---|---|---|---|---|---|---|---|---|
| cgt | gac | cca | cta | gag | ttt | cga | ccg | gaa | cgg | ttc | tct | gaa | gac | gat | gtc | 1304 |
| Arg | Asp | Pro | Leu | Glu | Phe | Arg | Pro | Glu | Arg | Phe | Ser | Glu | Asp | Asp | Val |
| | 405 | | | | | 410 | | | | | 415 | | | | |

| | | | | | | | | | | | | | | | |
|---|---|---|---|---|---|---|---|---|---|---|---|---|---|---|---|
| gac | atg | aaa | ggt | cac | gat | tat | agg | cta | ctg | ccg | ttt | ggt | gca | ggg | agg | 1352 |
| Asp | Met | Lys | Gly | His | Asp | Tyr | Arg | Leu | Leu | Pro | Phe | Gly | Ala | Gly | Arg |
| 420 | | | | | 425 | | | | | 430 | | | | | 435 |

| | | | | | | | | | | | | | | |
|---|---|---|---|---|---|---|---|---|---|---|---|---|---|---|---|
| cgt | gtt | tgc | ccc | ggt | gca | caa | ctt | ggc | atc | aat | ttg | gtc | aca | tcc | atg | 1400 |
| Arg | Val | Cys | Pro | Gly | Ala | Gln | Leu | Gly | Ile | Asn | Leu | Val | Thr | Ser | Met |
| | | | | 440 | | | | 445 | | | | | 450 | | |

| | | | | | | | | | | | | | | | |
|---|---|---|---|---|---|---|---|---|---|---|---|---|---|---|---|
| atg | ggt | cac | cta | ttg | cac | cat | ttc | tat | tgg | agc | cct | cct | aaa | ggt | gta | 1448 |
| Met | Gly | His | Leu | Leu | His | His | Phe | Tyr | Trp | Ser | Pro | Pro | Lys | Gly | Val |
| | | | | 455 | | | | 460 | | | | | 465 | | |

| | | | | | | | | | | | | | | | |
|---|---|---|---|---|---|---|---|---|---|---|---|---|---|---|---|
| aaa | cca | gag | gag | att | gac | atg | tca | gag | aat | cca | gga | ttg | gtc | acc | tac | 1496 |
| Lys | Pro | Glu | Glu | Ile | Asp | Met | Ser | Glu | Asn | Pro | Gly | Leu | Val | Thr | Tyr |
| | | 470 | | | | | 475 | | | | | 480 | | | |

| | | | | | | | | | | | | | | | |
|---|---|---|---|---|---|---|---|---|---|---|---|---|---|---|---|
| atg | cga | acc | ccg | gtg | caa | gct | gtt | ccc | act | cca | agg | ctg | cct | gct | cac | 1544 |
| Met | Arg | Thr | Pro | Val | Gln | Ala | Val | Pro | Thr | Pro | Arg | Leu | Pro | Ala | His |
| | 485 | | | | | 490 | | | | | 495 | | | | |

| | | | | | | | | |
|---|---|---|---|---|---|---|---|---|
| ttg | tac | aaa | cgt | gta | gct | gtg | gat | atg | taattcttag tttgttatta | 1591 |
| Leu | Tyr | Lys | Arg | Val | Ala | Val | Asp | Met |
| 500 | | | | | 505 | | | |

Fig. 4C

SEQ ID 1

```
ttcatgctct taaggttttg gactttgaac ttatgatgag atttgtaaaa ttccaagtga  1651
tcaaatgaag aaaagaccaa ataaaaaggc ttgacgattt aaaaaaaaaa aaaaaaa     1708
```

Fig. 4D

SEQ ID 2

| | | | | | | | | | | | | | | |
|---|---|---|---|---|---|---|---|---|---|---|---|---|---|---|
|Met|Ala|Phe|Leu|Leu|Ile|Pro|Ile|Ser|Ile|Ile|Phe|Ile|Val|Leu|Ala|
|1| | | |5| | | | |10| | | | |15|

Tyr Gln Leu Tyr Gln Arg Leu Arg Phe Lys Leu Pro Pro Gly Pro Arg
              20                  25                30

Pro Trp Pro Ile Val Gly Asn Leu Tyr Asp Ile Lys Pro Val Arg Phe
          35                  40                45

Arg Cys Phe Ala Glu Trp Ser Gln Ala Tyr Gly Pro Ile Ile Ser Val
      50                  55                60

Trp Phe Gly Ser Thr Leu Asn Val Ile Val Ser Asn Ser Glu Leu Ala
65                  70                  75                  80

Lys Glu Val Leu Lys Glu Lys Asp Gln Gln Leu Ala Asp Arg His Arg
              85                  90                  95

Ser Arg Ser Ala Ala Lys Phe Ser Arg Asp Gly Gln Asp Leu Ile Trp
                100                 105                 110

Ala Asp Tyr Gly Pro His Tyr Val Lys Val Thr Lys Val Cys Thr Leu
          115                 120                 125

Glu Leu Phe Thr Pro Lys Arg Leu Glu Ala Leu Arg Pro Ile Arg Glu
      130                 135                 140

Asp Glu Val Thr Ala Met Val Glu Ser Ile Phe Asn Asp Thr Ala Asn
145                 150                 155                 160

Pro Glu Asn Tyr Gly Lys Ser Met Leu Val Lys Lys Tyr Leu Gly Ala
              165                 170                 175

Val Ala Phe Asn Asn Ile Thr Arg Leu Ala Phe Gly Lys Arg Phe Val
          180                 185                 190

Asn Ser Glu Gly Val Met Asp Glu Gln Gly Leu Glu Phe Lys Glu Ile
      195                 200                 205

Val Ala Asn Gly Leu Lys Leu Gly Ala Ser Leu Ala Met Ala Glu His
      210                 215                 220

Ile Pro Trp Leu Arg Trp Met Phe Pro Leu Glu Glu Gly Ala Phe Ala
225                 230                 235                 240

Fig. 4E

SEQ ID 2

| | | | | | | | | | | | | | |
|---|---|---|---|---|---|---|---|---|---|---|---|---|---|
|Lys|His|Gly|Ala|Arg|Arg|Asp|Arg|Leu|Thr|Arg|Ala|Ile|Met|Glu|Glu|

Lys His Gly Ala Arg Arg Asp Arg Leu Thr Arg Ala Ile Met Glu Glu
                245                 250                 255

His Thr Ile Ala Arg Lys Lys Ser Gly Gly Ala Gln Gln His Phe Val
            260                 265                 270

Asp Ala Leu Leu Thr Leu Gln Glu Lys Tyr Asp Leu Ser Glu Asp Thr
            275                 280                 285

Ile Ile Gly Leu Leu Trp Asp Met Ile Thr Ala Gly Met Asp Thr Thr
    290                 295                 300

Ala Ile Ser Val Glu Trp Ala Met Ala Glu Leu Ile Lys Asn Pro Arg
305                 310                 315                 320

Val Gln Gln Lys Ala Gln Glu Glu Leu Asp Asn Val Leu Gly Ser Glu
            325                 330                 335

Arg Val Leu Thr Glu Leu Asp Phe Ser Ser Leu Pro Tyr Leu Gln Cys
            340                 345                 350

Val Ala Lys Glu Ala Leu Arg Leu His Pro Pro Thr Pro Leu Met Leu
        355                 360                 365

Pro His Arg Ala Asn Ala Asn Val Lys Ile Gly Gly Tyr Asp Ile Pro
    370                 375                 380

Lys Gly Ser Asn Val His Val Asn Val Trp Ala Val Ala Arg Asp Pro
385                 390                 395                 400

Ala Val Trp Arg Asp Pro Leu Glu Phe Arg Pro Glu Arg Phe Ser Glu
            405                 410                 415

Asp Asp Val Asp Met Lys Gly His Asp Tyr Arg Leu Leu Pro Phe Gly
            420                 425                 430

Ala Gly Arg Arg Val Cys Pro Gly Ala Gln Leu Gly Ile Asn Leu Val
        435                 440                 445

Thr Ser Met Met Gly His Leu Leu His His Phe Tyr Trp Ser Pro Pro
    450                 455                 460

Lys Gly Val Lys Pro Glu Glu Ile Asp Met Ser Glu Asn Pro Gly Leu
465                 470                 475                 480

Fig. 4F

SEQ ID 2

Val Thr Tyr Met Arg Thr Pro Val Gln Ala Val Pro Thr Pro Arg Leu
                485             490                495

Pro Ala His Leu Tyr Lys Arg Val Ala Val Asp Met
            500             505

Fig. 4G

SEQ ID 3

<400> 3

```
tgcaaacctg cacaaacaaa gagagagaag aagaaaaagg aagagaggag agagagagag    60
agagagagaa gcc atg gat tct tct ctt cat gaa gcc ttg caa cca cta      109
            Met Asp Ser Ser Leu His Glu Ala Leu Gln Pro Leu
             1               5                  10 ccc atg acg ctg ttc ttc att ata cct ttg cta ctc tta ttg ggc cta    157
Pro Met Thr Leu Phe Phe Ile Ile Pro Leu Leu Leu Leu Leu Gly Leu
         15                  20                  25 gta tct cgg ctt cgc cag aga cta cca tac cca cca ggc cca aaa ggc    205
Val Ser Arg Leu Arg Gln Arg Leu Pro Tyr Pro Pro Gly Pro Lys Gly
         30                  35                  40 tta ccg gtg atc gga aac atg ctc atg atg gat caa ctc act cac cga    253
Leu Pro Val Ile Gly Asn Met Leu Met Met Asp Gln Leu Thr His Arg
 45                  50                  55                  60 gga ctc gcc aaa ctc gcc aaa caa tac gg  ggt cta ttc cac ctc aag    301
Gly Leu Ala Lys Leu Ala Lys Gln Tyr Gly Gly Leu Phe His Leu Lys
                 65                  70                  75 atg gga ttc tta cac atg gtg gcc gtt tcc aca ccc gac atg gct cgc    349
Met Gly Phe Leu His Met Val Ala Val Ser Thr Pro Asp Met Ala Arg
             80                  85                  90 caa gtc ctt caa gtc caa gac aac atc ttc tcg aac cgg cca gcc acc    397
Gln Val Leu Gln Val Gln Asp Asn Ile Phe Ser Asn Arg Pro Ala Thr
         95                  100                 105 ata gcc atc agc tac ctc acc tat gac cga gcc gac atg gcc ttc gct    445
Ile Ala Ile Ser Tyr Leu Thr Tyr Asp Arg Ala Asp Met Ala Phe Ala
     110                 115                 120 cac tac ggc ccg ttt tgg cgt cag atg cgt aaa ctc tgc gtc atg aaa    493
His Tyr Gly Pro Phe Trp Arg Gln Met Arg Lys Leu Cys Val Met Lys
125                 130                 135                 140 tta ttt agc cgg aaa cga gcc gag tcg tgg gag tcg gtc cga gac gag    541
Leu Phe Ser Arg Lys Arg Ala Glu Ser Trp Glu Ser Val Arg Asp Glu
                 145                 150                 155 gtc gac tcg gca gta cga gtg gtc gcg tcc aat att ggg tcg acg gtg    589
Val Asp Ser Ala Val Arg Val Val Ala Ser Asn Ile Gly Ser Thr Val
             160                 165                 170
```

Fig. 5A

SEQ ID 3

| | | | | | | | | | | | | | | | |
|---|---|---|---|---|---|---|---|---|---|---|---|---|---|---|---|
| aat | atc | ggc | gag | ctg | gtt | ttt | gct | ctg | acg | aag | aat | att | act | tac | agg | 637 |
| Asn | Ile | Gly | Glu | Leu | Val | Phe | Ala | Leu | Thr | Lys | Asn | Ile | Thr | Tyr | Arg |
| | | 175 | | | | 180 | | | | | 185 | | | | |

```
aat atc ggc gag ctg gtt ttt gct ctg acg aag aat att act tac agg     637
Asn Ile Gly Glu Leu Val Phe Ala Leu Thr Lys Asn Ile Thr Tyr Arg
        175             180                 185 gcg gct ttt ggg acg atc tcg cat gag gac cag gac gag ttc gtg gcc     685
Ala Ala Phe Gly Thr Ile Ser His Glu Asp Gln Asp Glu Phe Val Ala
        190             195                 200 ata ctg caa gag ttt tcg cag ctg ttt ggt gct ttt aat ata gct gat     733
Ile Leu Gln Glu Phe Ser Gln Leu Phe Gly Ala Phe Asn Ile Ala Asp
205             210             215                 220 ttt atc cct tgg ctc aaa tgg gtt cct cag ggg att aac gtc agg ctc     781
Phe Ile Pro Trp Leu Lys Trp Val Pro Gln Gly Ile Asn Val Arg Leu
                225             230                 235 aac aag gca cga ggg gcg ctt gat ggg ttt att gac aag atc atc gac     829
Asn Lys Ala Arg Gly Ala Leu Asp Gly Phe Ile Asp Lys Ile Ile Asp
            240             245                 250 gat cat ata cag aag ggg agt aaa aac tcg gag gag gtt gat act gat     877
Asp His Ile Gln Lys Gly Ser Lys Asn Ser Glu Glu Val Asp Thr Asp
            255             260                 265 atg gta gat gat tta ctt gct ttt tac ggt gag gaa gcc aaa gta agc     925
Met Val Asp Asp Leu Leu Ala Phe Tyr Gly Glu Glu Ala Lys Val Ser
        270             275                 280 gaa tct gac gat ctt caa aat tcc atc aaa ctc acc aaa gac aac atc     973
Glu Ser Asp Asp Leu Gln Asn Ser Ile Lys Leu Thr Lys Asp Asn Ile
285             290             295                 300 aaa gct atc atg gac gta atg ttt gga ggg acc gaa acg gtg gcg tcc    1021
Lys Ala Ile Met Asp Val Met Phe Gly Gly Thr Glu Thr Val Ala Ser
                305             310                 315 gcg att gaa tgg gcc atg acg gag ctg atg aaa agc cca gaa gat cta    1069
Ala Ile Glu Trp Ala Met Thr Glu Leu Met Lys Ser Pro Glu Asp Leu
            320             325                 330 aag aag gtc caa caa gaa ctc gcc gtg gtg gtg ggt ctt gac cgg cga    1117
Lys Lys Val Gln Gln Glu Leu Ala Val Val Val Gly Leu Asp Arg Arg
        335             340                 345
```

Fig. 5B

SEQ ID 3

```
gtc gaa gag aaa gac ttc gag aag ctc acc tac ttg aaa tgc gta ctg    1165
Val Glu Glu Lys Asp Phe Glu Lys Leu Thr Tyr Leu Lys Cys Val Leu
350             355                 360 aag gaa gtc ctt cgc ctc cac cca ccc atc cca ctc ctc ctc cac gag    1213
Lys Glu Val Leu Arg Leu His Pro Pro Ile Pro Leu Leu Leu His Glu
365             370                 375                 380 act gcc gag gac gcc gag gtc ggc ggc tac tac att ccg gcg aaa tcg    1261
Thr Ala Glu Asp Ala Glu Val Gly Gly Tyr Tyr Ile Pro Ala Lys Ser
                385                 390                 395 cgg gtg atg atc aac gcg tgc gcc atc ggc cgg gac aag aac tcg tgg    1309
Arg Val Met Ile Asn Ala Cys Ala Ile Gly Arg Asp Lys Asn Ser Trp
                400                 405                 410 gcc gac cca gat acg ttt agg ccc tcc agg ttt ctc aaa gac ggt gtg    1357
Ala Asp Pro Asp Thr Phe Arg Pro Ser Arg Phe Leu Lys Asp Gly Val
                415                 420                 425 ccc gat ttc aaa ggg aac aac ttc gag ttc atc cca ttc ggg tca ggt    1405
Pro Asp Phe Lys Gly Asn Asn Phe Glu Phe Ile Pro Phe Gly Ser Gly
        430                 435                 440 cgt cgg tct tgc ccc ggt atg caa ctc gga ctc tac gcg cta gag acg    1453
Arg Arg Ser Cys Pro Gly Met Gln Leu Gly Leu Tyr Ala Leu Glu Thr
445                 450                 455                 460 act gtg gct cac ctc ctt cac tgt ttc acg tgg gag ttg ccg gac ggg    1501
Thr Val Ala His Leu Leu His Cys Phe Thr Trp Glu Leu Pro Asp Gly
                465                 470                 475 atg aaa ccg agt gaa ctc gag atg aat gat gtg ttt gga ctc acc gcg    1549
Met Lys Pro Ser Glu Leu Glu Met Asn Asp Val Phe Gly Leu Thr Ala
                480                 485                 490 cca aga gcg att cga ctc acc gcc gtg ccg agt cca cgc ctt ctc tgt    1597
Pro Arg Ala Ile Arg Leu Thr Ala Val Pro Ser Pro Arg Leu Leu Cys
        495                 500                 505 cct ctc tat tgatcgaatg attgggggag ctttgtggag gggcttttat            1646
Pro Leu Tyr
        510
```

Fig. 5C

SEQ ID 3

```
ggagactcta tatatagatg ggaagtgaaa caacgacagg tgaatgcttg gatttttggt 1706 atatattggg gagggagggg aaaaaaaaaa taatgaaagg aaagaaaaga gagaatttga 1766 atttctcttc ctctgtggat aaaagcctcg tttttaattg tttttatgtg gagatatttg 1826 tgtttgttta ttttatctc tttttttgca ataacactca aaataaaaa aaaaaa     1883
```

Fig. 5D

SEQ ID 4

<400> 4

| Met | Asp | Ser | Ser | Leu | His | Glu | Ala | Leu | Gln | Pro | Leu | Pro | Met | Thr | Leu |
| 1 | | | | 5 | | | | | 10 | | | | | 15 | |

| Phe | Phe | Ile | Ile | Pro | Leu | Leu | Leu | Leu | Leu | Gly | Leu | Val | Ser | Arg | Leu |
| | | | 20 | | | | | 25 | | | | | 30 | | |

| Arg | Gln | Arg | Leu | Pro | Tyr | Pro | Pro | Gly | Pro | Lys | Gly | Leu | Pro | Val | Ile |
| | | 35 | | | | | 40 | | | | | 45 | | | |

| Gly | Asn | Met | Leu | Met | Met | Asp | Gln | Leu | Thr | His | Arg | Gly | Leu | Ala | Lys |
| | 50 | | | | | 55 | | | | | 60 | | | | |

| Leu | Ala | Lys | Gln | Tyr | Gly | Gly | Leu | Phe | His | Leu | Lys | Met | Gly | Phe | Leu |
| 65 | | | | | 70 | | | | | 75 | | | | | 80 |

| His | Met | Val | Ala | Val | Ser | Thr | Pro | Asp | Met | Ala | Arg | Gln | Val | Leu | Gln |
| | | | | 85 | | | | | 90 | | | | | 95 | |

| Val | Gln | Asp | Asn | Ile | Phe | Ser | Asn | Arg | Pro | Ala | Thr | Ile | Ala | Ile | Ser |
| | | | 100 | | | | | 105 | | | | | 110 | | |

| Tyr | Leu | Thr | Tyr | Asp | Arg | Ala | Asp | Met | Ala | Phe | Ala | His | Tyr | Gly | Pro |
| | | 115 | | | | | 120 | | | | | 125 | | | |

| Phe | Trp | Arg | Gln | Met | Arg | Lys | Leu | Cys | Val | Met | Lys | Leu | Phe | Ser | Arg |
| | 130 | | | | | 135 | | | | | 140 | | | | |

| Lys | Arg | Ala | Glu | Ser | Trp | Glu | Ser | Val | Arg | Asp | Glu | Val | Asp | Ser | Ala |
| 145 | | | | | 150 | | | | | 155 | | | | | 160 |

| Val | Arg | Val | Val | Ala | Ser | Asn | Ile | Gly | Ser | Thr | Val | Asn | Ile | Gly | Glu |
| | | | | 165 | | | | | 170 | | | | | 175 | |

| Leu | Val | Phe | Ala | Leu | Thr | Lys | Asn | Ile | Thr | Tyr | Arg | Ala | Ala | Phe | Gly |
| | | | 180 | | | | | 185 | | | | | 190 | | |

| Thr | Ile | Ser | His | Glu | Asp | Gln | Asp | Glu | Phe | Val | Ala | Ile | Leu | Gln | Glu |
| | | 195 | | | | | 200 | | | | | 205 | | | |

| Phe | Ser | Gln | Leu | Phe | Gly | Ala | Phe | Asn | Ile | Ala | Asp | Phe | Ile | Pro | Trp |
| | 210 | | | | | 215 | | | | | 220 | | | | |

| Leu | Lys | Trp | Val | Pro | Gln | Gly | Ile | Asn | Val | Arg | Leu | Asn | Lys | Ala | Arg |
| 225 | | | | | 230 | | | | | 235 | | | | | 240 |

Fig. 5E

SEQ ID 4

Gly Ala Leu Asp Gly Phe Ile Asp Lys Ile Ile Asp Asp His Ile Gln
                245                 250                 255

Lys Gly Ser Lys Asn Ser Glu Glu Val Asp Thr Asp Met Val Asp Asp
            260                 265                 270

Leu Leu Ala Phe Tyr Gly Glu Glu Ala Lys Val Ser Glu Ser Asp Asp
            275                 280                 285

Leu Gln Asn Ser Ile Lys Leu Thr Lys Asp Asn Ile Lys Ala Ile Met
            290                 295                 300

Asp Val Met Phe Gly Gly Thr Glu Thr Val Ala Ser Ala Ile Glu Trp
305                 310                 315                 320

Ala Met Thr Glu Leu Met Lys Ser Pro Glu Asp Leu Lys Lys Val Gln
                325                 330                 335

Gln Glu Leu Ala Val Val Val Gly Leu Asp Arg Arg Val Glu Glu Lys
            340                 345                 350

Asp Phe Glu Lys Leu Thr Tyr Leu Lys Cys Val Leu Lys Glu Val Leu
            355                 360                 365

Arg Leu His Pro Pro Ile Pro Leu Leu Leu His Glu Thr Ala Glu Asp
370                 375                 380

Ala Glu Val Gly Gly Tyr Tyr Ile Pro Ala Lys Ser Arg Val Met Ile
385                 390                 395                 400

Asn Ala Cys Ala Ile Gly Arg Asp Lys Asn Ser Trp Ala Asp Pro Asp
                405                 410                 415

Thr Phe Arg Pro Ser Arg Phe Leu Lys Asp Gly Val Pro Asp Phe Lys
            420                 425                 430

Gly Asn Asn Phe Glu Phe Ile Pro Phe Gly Ser Gly Arg Arg Ser Cys
            435                 440                 445

Pro Gly Met Gln Leu Gly Leu Tyr Ala Leu Glu Thr Thr Val Ala His
            450                 455                 460

Leu Leu His Cys Phe Thr Trp Glu Leu Pro Asp Gly Met Lys Pro Ser
465                 470                 475                 480

Fig. 5F

SEQ ID 4

Glu Leu Glu Met Asn Asp Val Phe Gly Leu Thr Ala Pro Arg Ala Ile
            485             490             495

Arg Leu Thr Ala Val Pro Ser Pro Arg Leu Leu Cys Pro Leu Tyr
            500             505             510

Fig. 5G

SEQ ID 10

<400> 10

```
aaacaccaat ttaatgggat ttcagattng tatcccatgc tattggctaa ggcattttc   60
ttattgtaat ctaaccaatt ctaatttcca ccctggtgtg aactgactga caaatgcggt  120
ccgaaaacag cgaatgaaat gtctgggtga tcggtcaaac aagcggtggg cgagagagcg  180
cgggtgttgg cctagccggg atgggggtag gtagacggcg tattaccggc gagttgtccg  240
aatggagttt tcggggtagg tagtaacgta gacgtcaatg gaaaagtca taatctccgt   300
caaaaatcca accgctcctt cacatcgcag agttggtggc cacgggaccc tccacccact  360
cactcaatcg atcgcctgcc gtggttgccc attattcaac catacgccac ttgactcttc   420
accaacaatt ccaggccggc tttctataca atgtactgca caggaaaatc caatataaaa  480
agccggcctc tgcttccttc tcagtagccc ccagctcatt caattcttcc cactgcaggc  540
tacatttgtc agacacgttt tccgccattt ttcgcctgtt tctgcggaga atttgatcag  600
gttcggattg ggattgaatc aattgaaagg tttttatttt cagtatttcg atcgccatg   659
```

Fig. 6

SEQ ID 11

<400> 11

```
ggccgggtgg tgacatttat tcataaattc atctcaaaac aagaaggatt tacaaaaata  60
aaagaaaaca aaattttcat ctttaacata attataattg tgttcacaaa attcaaactt 120
aaaccettaa tataaagaat ttctttcaac aatacacttt aatcacaact tcttcaatca 180
caacctcctc caacaaaatt aaaatagatt aataataaa taaacttaac tatttaaaaa 240
aaaatattat acaaaattta ttaaaacttc aaaataaaca aacttttat acaaaattca 300
tcaaaacttt aaaataaagc taaacactga aaatgtgagt acatttaaaa ggacgctgat 360
cacaaaaatt ttgaaaacat aaacaaactt gaaactctac cttttaagaa tgagtttgtc 420
gtctcattaa ctcattagtt ttatagttcg aatccaatta acgtatcttt tattttatgg 480
aataagggtg ttttaataag tgattttggg atttttttag taatttattt gtgatatgtt 540
atggagtttt taaaaatata tatatatata tatatttttg ggttgagttt acttaaaatt 600
tggaaaaggt tggtaagaac tataaattga gttgtgaatg agtgttttat ggattttta 660
agatgttaaa tttatatatg taattaaaat tttattttga ataacaaaaa ttataattgg 720
ataaaaaatt gttttgttaa atttagagta aaaatttcaa aatctaaaat aattaaacac 780
tattatttt aaaaaatttg ttggtaaatt ttatcttata tttaagttaa aatttagaaa 840
aaattaattt taaattaata aacttttgaa gtcaaatatt ccaaatattt tccaaaatat 900
taaatctatt ttgcattcaa aatacaattt aataataaa acttcatgga atagattatc 960
caatttgtat aaaaaccaaa aatctcaaat aaaatttaaa ttacaaaaca ttatcaacat 1020
tatgatttca agaaagacaa taaccagttt ccaataaaat aaaaaacctc atggcccgta 1080
attaagatct cattaattaa ttcttatttt ttaattttt tacataqaaa atatctttat 1140
attgtatcca agaaatatag aatgttctcg tccagggact attaatctcc aaacaagttt 1200
caaatcatt acattaaagc tcatcatgtc atttgtggat tggaaattat attgtataag 1260
agaaatatag aatgttctcg tctagggact attaattcc aaacaaattt caaaatcatt 1320
```

Fig. 7A

SEQ ID 11

```
acattaaagc tcatcatgtc atttgtggat tggaaattag acaaaaaaaa tcccaaatat 1380
ttctctcaat ctcccaaaat atagttcgaa ctccatattt ttggaaattg agaatttttt 1440
tacccaataa tatatttttt tatacatttt agagattttc cagacatatt tgctctggga 1500
tttattggaa tgaaggttga gttataaact ttcagtaatc caagtatctt cggttttga 1560
agatactaaa tccattatat aataaaaaca cattttaaac accaatttaa tgggatttca 1620
gatttgtatc ccatgctatt ggctaaggca ttttttcttat tgtaatctaa ccaattctaa 1680
tttccaccct ggtgtgaact gactgacaaa tgcggtccga aaacagcgaa tgaaatgtct 1740
gggtgatcgg tcaancaagc ggtgggcgag agagcgcggg tgttggccta gccgggatgg 1800
gggtaggtag acggcgtatt accggcgagt tgtccgaatg gagttttcgg ggtaggtagt 1860
aacgtagacg tcaatggaaa aagtcataat ctccgtcaaa aatccaaccg ctccttcaca 1920
tcgcagagtt ggtggccacg ggaccctcca cccactcact cgatcgcctg ccgtggttgc 1980
ccattattca accatacgcc acttgactct tcaccaacaa ttccaggccg gctttctata 2040
caatgtactg cacaggaaaa tccaatataa aaagccggcc tctgcttcct tctcagtagc 2100
ccccagctca ttcaattctt cccactgcag gctacatttg tcagacacgt tttccgccat 2160
ttttcgcctg tttctgcgga gaatttgatc aggttcggat tgggattgaa tcaattgaaa 2220
ggttttattt ttcagtattt cgatcgccat g                             2251
```

Fig. 7B

SEQ ID 9

<400> 9

```
aaagataata tatgtgtatg cctactacta cacattgttt tgaagtgtgt aaacatagtg   60
caacactagg aggactcaca atgagcactt gttgacatga aactagctaa atgcccaaca  120
ataatagtga aagctagtta aactaacccc tttgactttc aagatgatat atttatatcc  180
ctactacgtc ttcctctttt tgtctttctc ttgtgattaa accttccttg aaacaattct  240
caaatgtaaa attaaacctt gaacttgta gagaccaaac ttccctagga gaaccacat    300
ttatgacaac atatatacac caacccattg catactataa tattggaatt acctgcagcg  360
aacgaaagaa acgctgtctc accaactcgt gcactacatc ccgaaactta accttcccct  420
gatacagatt gaagagccga aaaagcgtg catccaaatt tctggtatgg tgaggagccg   480
aaaaacgcgt gcgcctaatt ttttgagat gggccggaaa ataatgcgtg catctaaatt   540
ttcacgtgtc gcgtattggc gaggttgcgc tgaatgtgat cctgtgcgtg agccacattc  600
attccattgg ttgacccgcc ggtaccgcga ggaccgtggg gtctcacaga tacgcggatg  660
gtggatcagc actgagaaga ttagatgatg accaggcggg catttgaagt aaaaacttgg  720
gggtggttgg caagtacgcg acaaagaggg gtagtgcgca aggaagcgag ttggatgcaa  780
ataatattac aaagtgggtt ggtgggcatg agcatcaacc agaatgatgt tgttgctggt  840
tccgtgcaaa ttctgaccag tagtttgaac aatactaccc aacttgtttt tggtaaaaca  900
tgaagtgggt aaggagaatt gaacttacgt ctcatggtaa agggcaaggg caaatgactt  960
aacacatacc tttaactaat aaaaataccc ctaacaaata cgaaaacgaa tgagttatca 1020
cagaccttca actaataaga tagccatcag acccacatct cctgactgac caaaaacaaa 1080
tgacttcaac caactaagat acccatcaaa gctaacccac aacccaattc ctcacttccc 1140
cttaccagac caaccaagca gacctacgcc attaactact ttaggacgtg ggaattgggg 1200
gtgccaccgt tgaagaatgg cactcagggt tggtaatccc tccacgtgta tgtagcagtc 1260
gtttggtgga gacggcgtgt ttgaatgtcc accttccagt ttggagaaca aggaaattgg 1320
```

Fig. 8A

SEQ ID 9

```
gcttatatta ggcctggatc tcttgtttca gagcaggagt agttcaggac aggaactagc 1380
attcaagaat tcaattgccc tgccctgctc tgctctgctt tgctcaactt attgatccct 1440
gctctggttt gttcaatttc ttgacccctg ctgggttctg ctctggtttg cacactttct 1500
cgattatata agtcattttg gatccttgca aggaagagaa tatg              1544
```

Fig. 8B

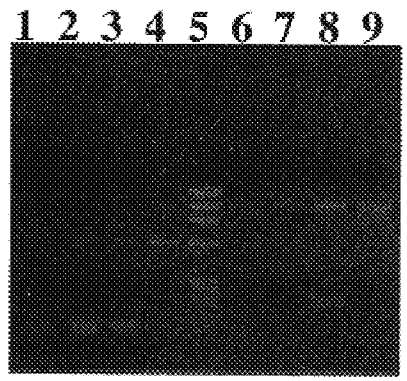

Lanes 1-4: PCR amplification of Sweetgum P450-1 gene from control and transgenic loblolly pine cell lines. Note the 600 bp amplified fragment in lanes 2-4.

Lanes 6-9: PCR amplification of Hygromycin gene from control and transgenic loblolly pine cell lines. Note the 1000 bp amplified fragment in lanes 7-9.

Lane 1: Control PT52 line
Lane 2: Transgenic line Y2
Lane 3: Transgenic line Y17
Lane 4: Control plasmid pSSLsP450-1-iml-s
Lane 5: DNA size marker Phi 174/HaeII (BRL); top 4 bands indicate molecular size of 1354, 1078, 872 and 603 bp.
Lane 6: Control PT52 line
Lane 7: Transgenic line Y7
Lane 8: Transgenic line O4
Lane 9: Control plasmid pHygro

FIG. 9

PRODUCTION OF SYRINGYL LIGNIN IN GYMNOSPERMS

FIELD OF THE INVENTION

This application claims the benefit of U.S. Provisional Application number 60/033,381, filed Dec. 16, 1996. The invention relates to the molecular modification of gymnosperms in order to cause the production of syringyl units during lignin biosynthesis and to production and propagation of gymnosperms contaniing syringyl lignin.

BACKGROUND OF THE INVENTION

Lignin is a major part of the supportive structure of most woody plants including angiosperm and gymnosperm trees which in turn are the principal sources of fiber for making paper and cellulosic products. In order to liberate fibers from wood structure in a manner suitable for making many grades of paper, it is necessary to remove much of the lignin from the fiberilignin network. Lignin is removed from wood chips by treatment of the chips in an alkaline solution at elevated temperatures and pressure in an initial step of papermaking processes. The rate of removal of lignin from wood of different tree species varies depending upon lignin structure. Three different lignin structures have been identified in trees: p-hydroxyphenyl, guaiacyl and syringyl, which are illustrated in FIG. 1.

Angiosperm species, such as *Liquidambar styraciflua* L. [sweetgum], have lignin composed of a mixture of guaiacyl and syringyl monomer units. In contrast, gymnosperm species such as *Pinus taeda* L. [loblolly pine] have lignin which is devoid of syringyl monomer units. Generally speaking, the rate of delignification in a pulping process is directly proportional to the amount of syringyl lignin present in the wood. The higher delignification rates associated with species having a greater proportion of syringyl lignin result in more efficient pulp mill operations since the mills make better use of energy and capital investment and the environmental impact is lessened due to a decrease in chemicals used for delignification.

It is therefore an object of the invention to provide gymnosperm species which are easier to delignify in pulping processes.

Another object of the invention is to provide gymnosperm species such as loblolly pine which contain syringyl lignin.

An additional object of the invention is to provide a method for modifying genes involved in lignin biosynthesis in gymnosperm species so that production of syringyl lignin is increased while production of guaiacyl lignin is suppressed.

Still another object of the invention is to produce whole gymnosperm plants containing genes which increase production of syringyl lignin and repress production of guaiacyl lignin.

Yet another object of the invention is to identify, isolate and/or clone those genes in angiosperms responsible for production of syringyl lignin.

A further object of the invention is to provide, in gymnosperms, genes which produce syringyl lignin.

Another object of the invention is to provide a method for making an expression cassette insertable into a gymnosperm cell for the purpose of inducing formation of syringyl lignin in a gymnosperm plant derived from the cell.

Definitions

The term "promoter" refers to a DNA sequence in the 5' flanking region of a given gene which is involved in recognition and binding of RNA polymerase and other transcriptional proteins and is required to initiate DNA transcription in cells.

The term "constitutive promoter" refers to a promoter which activates transcription of a desired gene, and is commonly used in creation of an expression cassette designed for preliminary experiments relative to testing of gene function. An example of a constitutive promoter is 35S CaMV, available from Clonetech.

The term "expression cassette" refers to a double stranded DNA sequence which contains both promoters and genes such that expression of a given gene is acheived upon insertion of the expression cassette into a plant cell.

The term "plant" includes whole plants and portions of plants, including plant organs (e.g. roots, stems, leaves, etc.)

The term "angiosperm" refers to plants which produce seeds encased in an ovary. A specific example of an angiosperm is *Liquidambar styraciflua* (L.)[sweetgum]. The angiosperm sweetgum produces syringyl lignin.

The term "gymnosperm" refers to plants which produce naked seeds, that is, seeds which are not encased in an ovary. A specific example of a gymnosperm is *Pinus taeda* (L.) [loblolly pine]. The gymnosperm loblolly pine does not produce syringyl lignin.

SUMMARY OF THE INVENTION

With regard to the above and other objects, the invention provides a method for inducing production of syringyl lignin in gymnosperms and to gymnosperms which contain syringyl lignin for improved delignification in the production of pulp for papermaking and other applications. In accordance with one of its aspects, the invention involves cloning an angiosperm DNA sequence which codes for enzymes involved in production of syringyl lignin monomer units, fusing the angiosperm DNA sequence to a lignin promoter region to form an expression cassette, and inserting the expression cassette into a gymnosperm genome.

Enzymes required for production of syringyl lignin in an angiosperm are obtained by deducing an amino acid sequence of the enzyme, extrapolating an MRNA sequence from the amino acid sequence, constructing a probe for the corresponding DNA sequence and cloning the DNA sequence which codes for the desired enzyme. A promoter region specific to a gymnosperm lignin biosynthesis gene is identified by constructing a probe for a gymnosperm lignin biosynthesis gene, sequencing the 5' flanking region of the DNA which encodes the gymnosperm lignin biosynthesis gene to locate a promoter sequence, and then cloning that sequence.

An expression cassette is constructed by fusing the angiosperm syringyl lignin DNA sequence to the gymnosperm promoter DNA sequence. Alternatively, the angiosperm syrinigyl lignin DNA is fused to a constitutive promoter to form an expression cassette. The expression cassette is inserted into the gymnosperm genome to transform the gymnosperm genome. Cells containing the transformed genome are selected and used to produce a transformed gymnosperm plant containing syringyl lignin.

In accordance with the invention, the angiosperm gene sequences bi-OMT, 4CL, P450-1 and P450-2 have been determined and isolated as associated with production of syringyl lignin in sweetgum and lignin promoter regions for the gymnosperm loblolly pine have been determined to be the 5' flanking regions for the 4CL1B, 4CL3B and PAL gymnosperm lignin genes. Expression cassettes containing sequences of selected genes from sweetgum have been inserted into loblolly pine embryogenic cells and presence of sweetgum genes associated with production of syringyl lignin has been confirmed in daughter cells of the resulting loblolly pine embryogenic cells.

The invention therefore enables production of gymnosperms such as loblolly pine containing genes which code for production of syringyl lignin, to thereby produce in such species syringyl lignin in the wood structure for enhanced pulpability.

BRIEF DESCRIPTION OF THE DRAWINGS

The above and other aspects of the invention will now be further described in the following detailed specification considered in conjunction with the following drawings in which:

FIGS. 2A–2E illustrate a bifunctional-O-methyl transferase (bi-OMT) gene sequence involved in the production of syringyl lignin in an angiosperm (SEQ ID 5 and 6);

FIGS. 3A–3G illustrate a 4-coumarate CoA ligase (4CL) gene sequence involved in the production of syringyl lignin in an angiosperm (SEQ ID 7 and 8);

FIGS. 4A–4G illustrate a ferulic acid-5-hydroxylase (P450-1) gene sequence involved in the production of syringyl lignin in an angiosperm (SEQ ID 1);

FIGS. 5A–5G illustrate a P450-2 gene sequence involved in the production of syringyl lignin in an angiosperm (SEQ ID 3 and 4);

FIG. 6 illustrates nucleotide sequences of the 5' flanking region of the loblolly pine 4CL1B gene showing the location of regulatory elements for lignin biosynthesis (SEQ ID 10);

FIGS. 7A–7B illustrate nucleotide sequences of the 5' flanking region of the loblolly pine 4CL3B gene showing the location of regulatory elements for lignin biosynthesis (SEQ ID 11);

FIGS. 8A–8B illustrates nucleotide sequences of the 5' flanking region of loblolly pine PAL gene showing the location of regulatory elements for lignin biosynthesis (SEQ ID 9);

FIG. 9 illustrates a PCR confirmation of the sweetgum P450-1 gene sequence in transgenic loblolly pine cells.

DETAILED DESCRIPTION OF THE INVENTION

Figure 1:
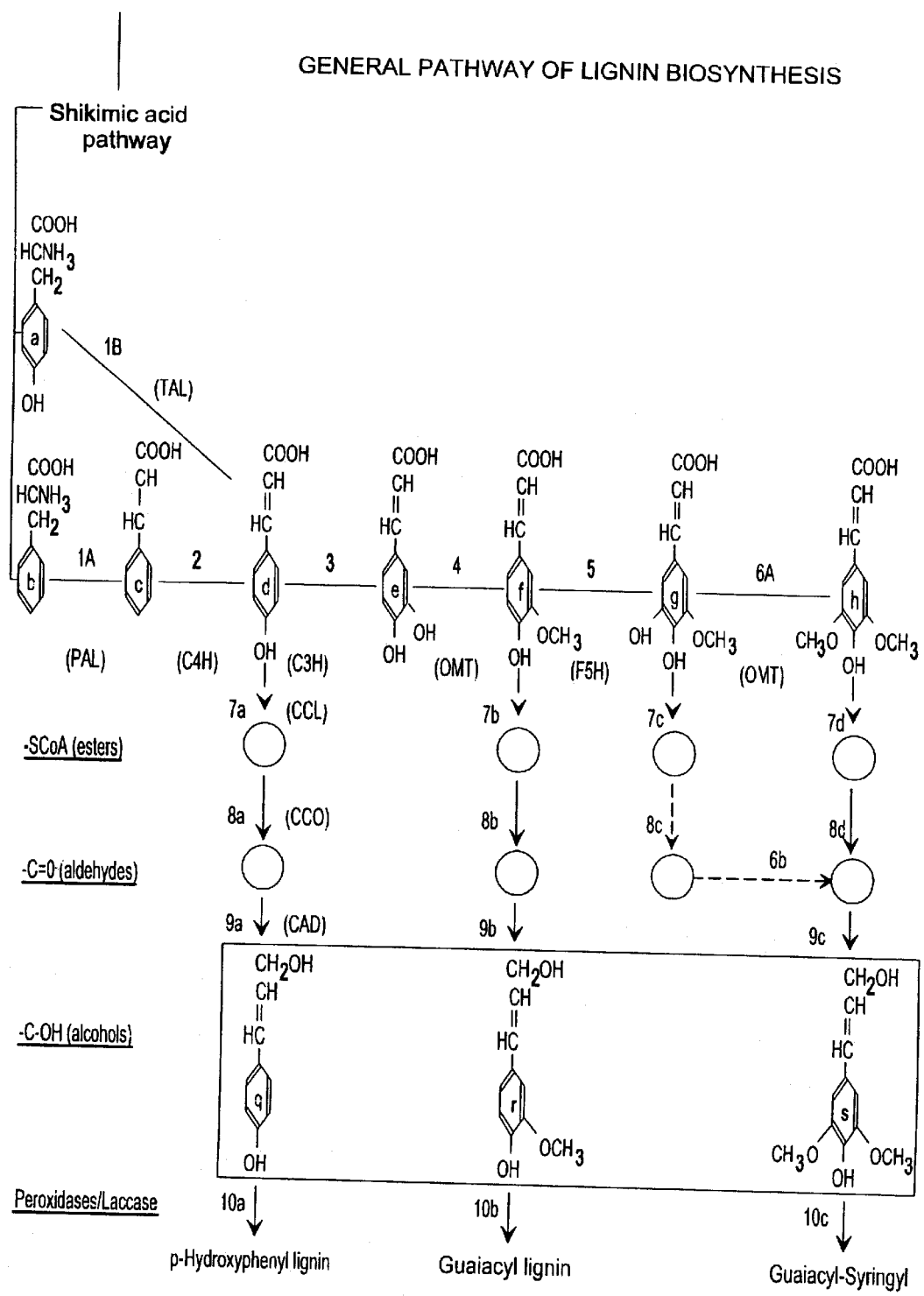
FIG. 1 illustrates a generalized pathway for lignin synthesis.

In accordance with the invention, a method is provided for modifying a gymnosperm genome, such as the genome of a loblolly pine, so that syringyl lignin will be produced in the resulting plant, thereby enabling cellulosic fibers of the same to be more easily separated from lignin in a pulping process. In general, this is accomplished by fusing one or more angiosperm DNA sequences (referred to at times herein as the "ASL DNA sequences") which are involved in production of syringyl lignin to a gymnosperm lignin promoter region (referred to at times herein as the "GL promoter region") specific to genes involved in gymnosperm lignin biosynthesis to form a gymnosperm syringyl lignin expression cassette (referred to at times herein as the "GSL expression cassette"). Alternatively, the one or more ASL DNA sequences are fused to one or more constitutive promoters to form a GSL expression cassette.

The GSL expression cassette preferably also includes selectable marker genes which enable transformed cells to be differentiated from untransformed cells. The GSL expression cassette containing selectable marker genes is inserted into the gymnosperm genome and transformed cells are identified and selected, from which whole gymnosperm plants may be produced which exhibit production of syringyl lignin.

To suppress production of less preferred forms of lignin in gymnosperms, such as guaiacyl lignin, genes from the gymnosperm associated with production of these less preferred forms of lignin are identified, isolated and the DNA sequence coding for anti-sense MnRNA (referred to at times herein as the "GL anti-sense sequence") for these genes is produced. The DNA sequence coding for anti-sense mRNA is then incorporated into the gymnosperm genome, which when expressed bind to the less preferred guaiacyl gymnosperm lignin mRNA, inactivating it.

Further features of these and various other steps and procedures associated with practice of the invention will now be described in more detail beginning with identification and isolation of ASL DNA sequences of interest for use in inducing production of syringyl lignin in a gymnosperm.

I. Determination of DNA Sequence For Genes Associated with Production of Syringyl Lignin The general biosynthetic pathway for production of lignin has been postulated as shown in FIG. 1. From FIG. 1, it can be seen that the genes CCL, OMT and F5H (which is from the class of P450 genes) may play key roles in production of syringyl lignin in some plant species, but their specific contributions and mechanisms remain to be positively established. It is suspected that the CCL, OMT and F5H genes may have specific equivalents in a specific angiosperm, such as sweetgum. Accordingly, one aim of the present invention is to identify, sequence and clone specific genes of interest from an angiosperm such as sweetgum which are involved in production of syringyl lignin and to then introduce those genes into the genome of a gymnosperm, such as loblolly pine, to induce production of syringyl ligin.

Genes of interest may be identified in various ways, depending on how much information about the gene is already known. Genes believed to be associated with production of syringyl lignin have already been sequenced from a few angiosperm species, viz, CCL and OMT.

DNA sequences of the various CCL and OMT genes are compared to each other to determine if there are conserved regions. Once the conserved regions of the DNA sequences are identified, primers homologous to the conserved sequences are synthesized. Reverse transcription of the DNA-free total RNA which was purified from sweetgum xylem tissue, followed by double PCR using gene-specific primers, enables production of probes for the CCL and OMT genes.

A sweetgum cDNA library is constructed in a host, such as lambda ZAPII, available from Stratagene, of LaJolla, Calif., using poly(A) +RNA isolated from sweetgun xylem, according to the methods described by Bugos et al. (1995 Biotechniques 19:734–737). The above mentioned probes are used to assay the sweetgum cDNA library to locate cDNA which codes for enzymes involved in production of syringyl lignin. Once a syringyl lignin sequence is located, it is then cloned and sequenced according to known methods which are familiar to those of ordinary skill.

In accordance with the invention, two sweetgum syringyl lignin genes have been determined using the above-described technique. These genes have been designated 4CL and bi-OMT. The sequence obtained for the sweetgum syringyl lignin gene, designated bi-OMT, is illustrated in FIG. 2 (SEQ ID 5 and 6). The sequence obtained for the sweetgum syringyl lignin gene, designated 4CL, is illustrated in FIG. 3 (SEQ ID 7 and 8).

An alternative procedure was employed to identify the F5H equivalent genes in sweetgum. Because the DNA sequences for similar P450 genes from other plant species were known, probes for the P450 genes were designed based on the conserved regions found by comparing the known sequences for similar P450 genes. The known P450 sequences used for comparison include all plant P450 genes in the GenBank database. Primers were designed based on two highly conserved regions which are common to all known plant P450 genes. The primers were then used in a PCR reaction with the sweetgum cDNA library as a template. Once P450-like fragments were located, they were amplified using standard PCR techniques, cloned into a pBluescript vector available from Stratagene LaJolla, Calif. and transformed into a DH5α E. coli strain available from Gibco BRL of Gaithersburg, Md.

After E. coli colonies were tested in order to determine that they contained the P450-like DNA fragments, the fragments were sequenced. Several P450-like sequences were located in sweetgum using the above described technique. One P450like sequence was sufficiently different from other known P450 sequences to indicate that it represented a new P450 gene family. This potentially new P450 cDNA fragment was used as a probe to screen two full length clones from the sweetgum xylme cDNA library. These putative hydroxylase clones were disignated P450-1 and P450-2. The sequence obtained for P450-1 and P450-2 are illustrated in FIG. 4 (SEQ ID No. 1 and 2 ) and FIG 5. (SEQ ID No. 3 and 4).

II. Identification of GL Gene Promoter Regions

In order to locate gymnosperm lignin promoter regions, probes are developed to locate lignin genes. After the gymnosperm lignin gene is located, the portion of DNA upstream from the gene is sequenced, preferably using the GenomeWalker Kit, available from Clontech. The portion of DNA upstream from the lignin gene will generally contain the gymnosperm lignin promoter region.

Gymnosperm genes of interest include CCL-like genes and PAL-like genes, which are beleived to be involved in the production of lignin in gymnosperms. Preferred probe sequences are developed based on previously sequenced genes, which are available from the gene bank. The preferred gene bank accession numbers for the CCL-like genes include U39404 and U39405. A preferred gene bank accession number for a PAL-like gene is U39792. Probes for such genes are constructed according to methods familiar to those of ordinary skill in the art. A genomic DNA library is constructed and DNA fragments which code for gymnosperm lignin genes are then identified using the above mentioned probes. A preferred DNA library is obtained from the gymnosperm, Pinus taeda (L.)[Loblolly Pine], and a preferred host of the genomic library is Lambda DashII, available from Stratagene of LaJolla, Calif.

Once the DNA fragments which code for the gymnosperm lignin genes are located, the genomic region upstream from the gymnosperm lignin gene (the 5' flanking region) was identified. This region contains the GL promoter. Three promoter regions were located from gymnosperm lignin biosynthesis genes. The first is the 5' flanking region of the loblolly pine 4CL1B gene, shown in FIG. 6 (SEQ ID 10). The second is the 5' flanking region of the loblolly pine gene 4CL3B, shown in FIG. 7 (SEQ ID 11). The third is the 5' flanking region of the loblolly pine gene PAL, shown in FIG. 8 (SEQ ID 9).

III. Fusing the GL Promoter Region to the ASL DNA Sequence

The next step of the process is to fuse the GL promoter region to the ASL DNA sequence to make a GSL expression cassette for insertion into the genome of a gymnosperm. This may be accomplished by standard techniques. In a preferred method, the GL promoter region is first cloned into a suitable vector. Preferred vectors are pGEM7Z, available from Promega, Madison, Wis. and SK available from Stratagene, of Lajolla, Calif. After the promoter sequence is cloned into the vector, it is then released with suitable restriction enzymes. The ASL DNA sequence is released with the same restriction enzyme(s) and purified.

The GL promoter region sequence and the ASL DNA sequence are then ligated such as with T4 DNA ligase, available from Promega, to form the GSL expression cassette. Fusion of the GL and ASL DNA sequence is confirmed by restriction enzyme digestion and DNA sequencing. After confirmation of GL promoter-ASL DNA fusion, the GSL expression cassette is released from the original vector with suitable restriction enzymes and used in construction of vectors for plant transformation.

IV. Fusing the ASL DNA Sequence to a Constitutive Promoter Region

In an alternative embodiment, a standard constitutive promoter may be fused with the ASL DNA sequence to make a GSL expression cassette. For example, a standard constitutive promoter may be fused with P450-1 to form an expression cassette for insertion of P450-1 sequences into a gymnosperm genome. In addition, a standard constitutive promoter may be fused with P450-2 to form an expression cassette for insertion of P450-2 into a gymnosperm genome. A constitutive promoter for use in the invention is the double 35S promoter.

In the preferred practice of the invention using constitutive promoters, a suitable vector such as pBI221, is digested by XbaI and HindIII to release the 35S promoter. At the same time the vector pHygro, available from International Paper, was digested by XbaI and HindIII to release the double 35S promoter. The double 35S promoter was ligated to the previously digested pBI221 vector to produce a new pBI221 with the double 35S promoter. This new pBI221 was digested with SacI and SmaI, to release the GUS fragment. The vector is next treated with T4 DNA polymerase to produce blunt ends and the vector is self-ligated. This vector is then further digested with BamHI and XbaI, available from Promega. After the pBI221 vector containing the constitutive promoter region has been prepared, lignin gene sequences are prepared for insertion into the pBI221 vector.

The coding regions of sweetgum P450-1 or P450-2 are amplified by PCR using primer with restriction sites incorporated in the 5' and 3' ends. In one example, an XbaI site was incorporated at the 5' end and a BamnHI site was incorporated at the 3' end of the sweetgum P450-1 or P450-2 genes. After PCR, the P450-1 and P450-2 genes were separately cloned into a TA vector available from Invitrogen. The TA vectors containing the P450-1 and P450-2 genes, respectively, were digested by XbaI and BamHI to release the P450-1 or P450-2 sequences.

The p35SS vector, described above, and the isolated sweetgum P450-1 or P450-2 fragments were then ligated to make GLS expression cassettes containing the constitutive promoter.

V. Inserting the Expression Cassette into the Gymnosperm Genome

There are a number of methods by which the GSL expression cassette may be inserted into a target gymnosperm cell. One method of inserting the expression cassette into the gymnosperm is by micro-projectile bombardment of gymnosperm cells. For example, embryogenic tissue cultures of loblolly pine may be initiated from immature zygotic embryos. Tissue is maintained in an undifferentiated state on semi-solid proliferation medium. For transformation, embryogenic tissue is suspended in liquid proliferation medium. Cells are then sieved through, a preferably 40 mesh screen, to separate small, densely cytoplasmic cells from large vacuolar cells.

After separation, a portion of the liquid cell suspension fraction is vacuum deposited onto filter paper and placed on semi-solid proliferation medium. The prepared gymnosperm target cells are then grown for several days on filter paper discs in a petri dish.

A 1:1 mixture of plasmid DNA containing the selectable marker expression cassette and plasmid DNA containing the P450-1 expression cassette may be precipitated with gold to form microprojectiles. The microprojectiles are rinsed in absolute ethanol and aliqots are dried onto a suitable macrocarrier such as the macrocarrier available from BioRad in Hercules, Calif.

Prior to bombardment, embryogenic tissue is preferably desiccated under a sterile laminar-flow hood. The desiccated tissue is transferred to semi-solid proliferation medium. The prepared microprojectiles are accelerated from the macrocarrier into the desiccated target cells using a suitable apparatus such as a BioRad PDS-1000/HE particle gun. In a preferred method, each plate is bombarded once, rotated 180 degrees, and bombarded a second time. Preferred bombardment parameters are 1350 psi rupture disc pressure, 6 mm distance from the rupture disc to macrocarrier (gap distance), 1 cm macrocarrier travel distance, and 10 cm distance from macrocarrier stopping screen to culture plate (microcarrier travel distance). Tissue is then transferred to semi-solid proliferation medium containing a selection agent, such as hygromycin B, for two days after bombardment.

Other methods of inserting the GSL expression cassette include use of silicon carbide whiskers, transformed protoplasts, Agrobacterium vectors and electroporation.

VI. Identifying Transformed Cells

In general, insertion of the GSL expression cassette will typically be carried out in a mass of cells and it will be necessary to determine which cells harbor the recombinant DNA molecule containing the GSL expression cassette. Transformed cells are first identified by their ability to grow vigorously on a medium containing an antibiotic which is toxic to non-transformed cells. Preferred antibiotics are kanamycin and hygromycin B. Cells which grow vigorously on antibiotic containing medium are further tested for presence of either portions of the plasmid vector, the syringyl lignin genes in the GSL expression cassette; e.g. the angiosperm bi-OMT, 4CL, P450-1 or P450-2 gene, or by testing for presence of other fragments in the GSL expression cassette. Specific methods which can be used to test for presence of portions of the GSL expression cassette include Southern blotting with a labeled complementary probe or PCR amplification with specific complementary primers. In yet another approach, an expressed syringyl lignin enzyme can be detected by Western blotting with a specific antibody, or by assaying for a functional property such as the appearance of functional enzymatic activity.

VII. Production of a Gymnosperm Plant from the Transformed Gymnosperm Cell

Once transformed embryogenic cells of the gymnosperm have been identified, isolated and multiplied, they may be grown into plants. It is expected that all plants resulting from transformed cells will contain the GSL expression cassette in all their cells, and that wood in the secondary growth stage of the mature plant will be characterized by the presence of syringyl lignin.

Transgenic embryogenic cells are allowed to replicate and develop into a somatic embryo, which are then converted into a somatic seedling.

VIII. Identification, Production and Insertion of a GL mRNA Anti-Sense Sequence

In addition to adding ASL DNA sequences, anti-sense sequences may be incorporated into a gymnosperm genome, via GSL expression cassettes, in order to suppress formation of the less preferred native gymnosperm lignin. To this end, the gymnosperm lignin gene is first located and sequenced in order to determine its nucleotide sequence. Methods for locating and sequencing amino acids which have been previously discussed may be employed. For example, if the gymnosperm lignin gene has already been purified, standard sequencing methods may be employed to determine the DNA nucleic acid sequence.

If the gymnosperm lignin gene has not been purified and functionally similar DNA or mRNA sequences from similar species are known, those sequences may be compared to identify highly conserved regions and this information used as a basis for the construction of a probe. A gymnosperm cDNA or genomic library can be probed with the above mentioned sequences to locate the gymnosperm lignin cDNA or genomic DNA. Once the gymnosperm lignin DNA is located, it may be sequenced using standard sequencing methods.

After the DNA sequence has been obtained for a gymnosperm lignin sequence, the complementary anti-sense strand is constructed and incorporated into an expression cassette. For example, the GL mRNA anti-sense sequence may be fused to a promoter region to form an expression cassette as described above. In a preferred method, the GL mRNA anti-sense sequence is incorporated into the previously discussed GSL expression cassette which is inserted into the gymnosperm genome as described above.

IX. Inclusion of Cytochrome P450 Reductase (CPR) to Enhance Biosynthesis of Syringyl Lignin in Gymnosperms In the absence of external cofactors such as NADPH (an electron donor in reductive biosyntheses), certain angiosperm lignin genes such as the P450 genes may remain inactive or not acheive full or desired activity after insertion into the genome of a gymnosperm. Inactivity or insufficient activity can be determined by testing the resulting plant which contains the P450 genes for the presence of syringyl lignin in secondary growth. It is known that cytochrome P450 reductase (CPR) may be involved in promoting certain reductive biochemical reactions, and may activate the desired expression of genes in many plants. Accordingly, if it is desired to enhance the expression of the angiosperm syringyl lignin genes in the gymnosperm, CPR may be inserted in the gymnosperm genome. In order to express CPR, the DNA sequence of the enzyme is ligated to a constitutive promoter or, for a specific species such as loblolly pine, xylem-specific lignin promoters such as PAL, 4CL1B or 4CL3B to form an expression cassette. The expression cassette may then be inserted into the gymnosperm genome by various methods as described above.

X. Examples

The following non-limiting examples illustrate further aspects of the invention. In these examples, the angiosperm is *Liquidambar styraciflua* (L.)[sweetgum] and the gymnosperm is *Pinus taeda* (L.)[loblolly pine]. The nomenclature for the genes referred to in the examples is as follows:

| Genes | Biochemical Name |
| --- | --- |
| 4CL (angiosperm) | 4-coumarate CoA ligase |
| bi-OMT (angiosperm) | bifunctional-O-methyl transferase |
| P450-1 (angiosperm) | Cytochrome P450 |
| P450-2 (angiosperm) | Cytochrome P450 |
| PAL (gymnosperm) | phenylalanine ammonia-lyase |
| 4CL1B (gymnosperm) | 4-coumarate CoA ligase |
| 4CL3B (gymnosperm) | 4-coumarate CoA ligase |

EXAMPLE 1

Isolating and Sequencing bi-OMT and 4CL Genes from an Angiosperm

A cDNA library for Sweetgum was constructed in Lambda ZAPII, available from Stratagene, of LaJolla, Calif., using poly(A) +RNA isolated from Sweetgum xylem tissue. Probes for bi-OMT and 4CL were obtained through reverse transcription of their mRNAs and followed by double PCR using gene-specific primers which were designed based on the OMT and CCL cDNA sequences obtained from similar genes cloned from other species.

Four primers were used for amplifying OMT fragments. One was an oligo-dT primer.One was a bi OMT primer (which was used to clone gene fragments through modified differential display technique, as described below in Example 2) and the other two were degenerate primers, which were based on the conserved sequences of all known OMTs. The two degenerate primers were derived based on the following amino acid sequences:

5'- Gly Gly Met Ala Thr Tyr Cys Cys Ala Thr Thr Tyr Ala Ala Cys Ala Ala Gly Gly Cys-3' (primer #22) (SEQ ID 12) and 3'-Ala Ala Ala Gly Ala Gly Ala Gly Asn Ala Cys Asn Asn Ala Asn Asn Ala Asn Gly Ala-5' (primer #23) (SEQ ID No. 13).

A 900 bp PCR product was produced when oligo-dT primer and primer #22 were used, and a 550 bp fragment was produced when primer numbers 22 aand 23 were used.

Three primers were used for amplifying CCL fragments. They were derived from the following amino acid sequences:

5'-Thr Thr Gly Gly Ala Thlr Cys Cys Gly Gly lie Ala Cys lie Ala Cys lie Gly Gly lie Tyr Thr Ile Cys Cys lie Ala Ala Mrg Gly Gly-3' (primer R1S) (SEQ ID No. 14)

5'-Thr Thr Gly Gly Ala Thr Cys Cys Gly Thr Hie Gly Thr i le Gly Cys lie Cys Ala Mg Cys Ala Mig Gly Thr fl e Gly Ala Tyr Gly Gly-3' (primer HIS) (SEQ ID No. 15) and 3'-Cys Cys Hie Cys Thr Tyr Thr Ala Asp Ala Cys Mrg Thr Ala Asp Gly Cys lie Cys Cys Ala Gly Cys Thlr Gly Thr Ala-5' (primer R2A) (SEQ ID No. 16)

R1S and H1S were both sense primers. Primer R2A was an anti-sense primer. A 650 bp fragment was produced if R1S and R2A primers were used and a 550 bp fragment was produced when primers H1S and R2A were used. The sequence of these three primers were derived from conserved sequences for plant CCLs.

The reverse transcription-double PCR cloning technique used for these examples consisted of adding 10 μg of DNA-free total RNA in 25 μl DEPC-treated water to a microfuge tube. Next, the following solutions were added:

a. 5×Reverse transcript buffer 8.0 μl, b. 0.1 MDTT 4.0 μl c. 10 mM dNTP 2.0 μl d. 100 μM oligo-dT primers 8.0 μl e. Rnasin 2.0 μl f. Superscript II 1.0 μl After mixing, the tube was incubated at a temperature of 42° C. for one (1) hour, followed by incubation at 70° C. for fifteen (15) minutes. Forty (40) μl of 1N NaOH was added and the tube was further incubated at 68° C. for twenty (20) minutes. After the incubation periods, 80 μl of 1N HCl was added to the reaction mixture. At the same time, 17 μl NaOAc, 5 μl glycogen and 768 μl of 100% ethanol were added and the reaction mixture was maintained at −80° C. for 15 minutes in order to precipitate the cDNA. The precipitated cDNA was centrifuged at high speed at 4° C. for 15 minutes. The resulting pellet was washed with 70% ethanol and then dried at room temperature, and then was dissolved in 20 μl of water.

The foregoing procedure produced purified cDNA which was used as a template to carry out first round PCR using primers #22 and oligo-dT for cloning OMT cDNA and primer R1S and R2A for cloning 4CL cDNA. For the first round PCR, a master mix of 50 μl for each reaction was prepared. Each 50 μl mixture contained:

a. 10×buffer 5 μl b. 25 mM MgCl₂5 μl c. 100 μM sense primer 1 μl (primer #22 for OMT and primer R1S for CCL).

d. 100 μl anti-sense primer 1 μl (oligo-dT primer for OMT and R2A for CCL).

e. 10 mM dNTP 1 μl f. Taq. DNA polymerase 0.5 μl

Of this master mix, 48 μl was added into a PCR tube containing 2 μl of cDNA for PCR. The tube was heated to 95° C. for 45 seconds, 52° C. for one minute and 72° C. for two minutes. This temperature cycle was repeated for 40 cycles and the mixture was then held at 72° C. for 10 minutes.

The cDNA fragments obtained from the first round of PCR were used as templates to perform the second round of PCR using primers 22 and 23 for cloning bi-OMT cDNA and primer H1S and R2A for cloning 4CL cDNA. The second round of PCR conditions were the same as the first round.

The desired cDNA fragment was then subcloned and sequenced. After the second round of PCR, the product with the predicted size was excised from the gel and ligated into a pUC19 vector, available from Clonetech, of Palo Alto, Calif., and then transformed into DH5α, an *E. coli* strain, available from Gibco BRL, of Gaithersburg, Md. After the inserts had been checked for correct size, the colonies were isolated and plasinids were sequenced using a Sequenase kit available from USB, of Cleveland, Ohio. The sequences are shown in FIG. 2 (SEQ ID 5 and 6) and FIG. 3 (SEQ ID 7 and 8).

EXAMPLE 2

Alternative Isolation Method of Angiosperm bi-OMT gene

As previously mentioned, one bi-OMT clone was produced via modified differential display technique. This method is another type of reverse transcription-PCR, in which DNA-free total RNA was reverse transcribed using oligo-dT primers with a single base pair anchor to form cDNA. The oligo-dT primers used for reverse transcription of mRNA to synthesize cDNA were:

T11A: TTTTTTTTTTTA (SEQ ID 17)

T11C: TTTTTTTTTTC (SEQ ID 18)

T11G: TTTTTTTTTTG (SEQ ID 19)

These cDNAs were then used as templates for radioactive PCR which was conducted in the presence of the same oligo-dT primers as listed above, a bi-OMT gene-specific primer and 35S-dATP. The OMT gene-specific primer was derived from the following amino acid sequence: 5'-Cys Cys Asn Gly Gly Asn Gly Gly Ser Ala Arg Gly Ala-3' (SEQ ID 20).

The following PCR reaction solutions were combined in a microfuge tube:

a. H$_2$O 9.2 µl, b. Taq Buffer 2.0 µl c. dNTP (25 µM) 1.6 µl d. Primers (5 µM) 2 µl, for each primer e. $^{35}$S-dATP 1 µl f. Taq. pol. 0.2 µl g. cDNA 2.0 µl The tube was heated to a temperature of 94° C. and held for 45 seconds, then at 37° C. for 2 minutes and then 72° C. for 45 seconds for forty cycles, followed by a final reaction at 72° C. for 5 minutes.

The amplified products were fractionated on a denaturing polyacrylamide sequencing gel and autoradiography was used to identify and excise the fragments with a predicted size. The designed OMT gene-specific primer had a sequence conserved in a region toward the 3'-end of the OMT cDNA sequence. This primer, together with oligo-dT, was amplified into a OMT cDNA fragment of about 300 bp.

Three oligo-dTs with a single base pair of A, C or G, respectively, were used to pair with the OMT gene-specific primer. Eight potential OMT cDNA fragments with predicted sizes of about 300 bp were excised from the gels after several independent PCR rounds using different combinations of oligo-dT and OMT gene-specific oligo-nucleotides as primers.

The OMT cDNA fragments were then re-amplified. A Southern blot analysis was performed for the resulting cDNAs using a 360 base-pair, $^{32}$P radio-isotope labeled, aspen OMT cDNA 3'-end fragment as a probe to identify the cDNA fragments having a strong hybridization signal, under low stringency conditions. Eight fragments were identified. Out of these eight cDNA fragments, three were selected based on their high hybridization signal for sub-cloning and sequencing. One clone, LsOMT3'-1, (where the "Ls" prefix indicates that the clone was derived from the *Liquidambar styraciflua* (L.) genome) was confirmed to encode bi-OMT based on its high homology to other lignin-specific plant OMTs at both nucleotide and amino acid sequence levels.

A cDNA library was constructed in Lambda ZAP II, available from Stratagene, of LaJolla, Calif., using 5 mg poly(A)+RNA isolated from sweetgum xylem tissue. The primary library consisting of approximately 0.7×10$^6$ independent recombinants was amplified and approximately 10$^5$ plaque-forming-units (pfu) were screened using a homologous 550 base-pair probe. The hybridized filter was washed at high stringency (0.25×SSC, 0.1% SDS, 65° C.) conditions. The colony containing the bi-OMT fragment identified by the probe was eluted and the bi-OMT fragment was produced. The sequence as illustrated in FIG. 2 (SEQ ID 5 and 6) was obtained.

EXMAPLE 3

Isolating and Producing the DNA which codes for the Angiosperm P450-1 Gene

In order to find putative P450 cDNA fragments as probes for cDNA library screening, a highly degenerated sense primer based on the amino acid sequence of 5'-Glu, Glu, Phe, Arg, Pro, Glu, Al2-3' (SEQ ID 21) was designed based on the conserved regions found in some plant P450 proteins. This conserved domain was located upstream of another highly conserved region in P450 proteins, which had an amino acid sequence of 5'-Phe Gly Xaa Gly Xaa Xaa Cys Xaa Gly-3' (SEQ ID 22). This primer was synthesized with the incorporation of an XboI restriction site to give a 26-base-pair oligomer.

This primer and the oligo-dT-XhoI primer were then used to perform PCR reactions with the sweetgum cDNA library as a template. The cDNA library was constructed in Lambda ZAPII, available from Stratagene, of LaJolla, Calif., using poly(A)+RNA isolated from Sweetgum xylem tissue. Amplified fragments of 300 to 600 bp were obtained. Because the designed primer was located upstream of the highly conserved P450 domain, this design distinguished whether the PCR products were P450 gene fragments depending on whether they contained the highly conserved amino acid domain.

All the fragments obtained from the PCR reaction were then cloned into a pUC19 vector, available from New England Biolab, Beverly, Mass., and transformed into a DH5α*E. coli* strain, available from Gibco BRL, of Gaithersburg, Md.

Twenty-four positive colonies were obtained and sequenced. Sequence analysis indicated four groupings within the twenty-four colonies. One was C4H, one was an unknown P450 gene, and two did not belong to P450 genes. Homologies of P450 genes in different species are usually more than 80%. Because the homologies between the P450 gene families found here were around 40%, the sequence analysis indicated that a new P450 gene family was sequenced. Moreover, since this P450 cDNA was isolated from xylem tissue, it was highly probable that this P450 gene was P450-1.

The novel sweetgum P450 cDNA fragment was used as a probe to screen a full length cDNA encoding for P450-1. Once the P450-1 gene was located it was sequenced. The length of the P450-1 cDNA is 1707 bp and it contains 45 bp of 5' non-coding region and 135 bp of 3' non-coding region. The deduced amino acid sequence also indicates that this P450 cDNA has a hydrophobic core at the N-terminal, which could be regarded as a leader sequence for c-translational targeting to membranes during protein synthesis. At the C-terminl region, there is a heme binding domain that is characteristic of all P450 genes. The P450-1 sequence, as illustrated in FIG. 4 (SEQ ID 1 and 2), was produced, according to the above described methods.

EXAMPLE 4

Isolating and Producing the DNA which codes for the Angiosperm P450-2 Gene

By using similar strategy of synthesizing PCR primers from the published literature for hydroxylase genes in plants, another full length P450 cDNA has been isolated that shows significant similarity with a putitive F5H clone from Arabidopsis (Meyers et al. 1996: PNAS 93, 6869–6874). This cloned cDNA, designated P450-2 contains 1883 bp and encodes an open reading frame of 511 amino acids. The amino acid similarity shared between Arabidopsis FSH and the P450-2 sweetgum clone is about 75%.

To confirm the function of the P450-2 gene, it was expressed in E. coli, strain, DH5 alpha, via pQE vector preparation, according to directions available with the kit. A $CO$—$Fe^{2+}$ binding assay was also performed to confirm the expression of P450-2 as a functional P450 gene. (Omura & Sato 1964, J. of Biochemistry 239: 2370–2378, Babriac et.al. 1991 Archives of Biochemistry and Biophysics 288:302–309). The $CO$—$Fe^{2+}$ binding assay showed a peak at 450nm which indicates that P450-2 has been overexpressed as a functional P450 gene.

The P450-2 protein was further purified for production of antibodies in rabbits, and antibodies have been successfully produced. In addition, Western blots show that this antibody is specific to the membrane fraction of sweetgum and aspen xylem extract. When the P450-2 antibody was added to a reaction mixture containing aspen xylem tissue, enzyme inhibition studies showed that the activity of FA5H in aspen was reduced more than 60%, a further indication that P450-2 performs a P450like function. Recombinant P450-2 protein co-expressed with Arabidopsis CPR protein in a baculovirus expression system hydroxylated ferulic acid (specific acvtivity:7.3 pKat/mg protein), cinnaminic acid (specific activity: 25 pKat/mg prtoein, and p-coumaric acid (specific activity 3.8 pKat/mg proten). The P450-2 enzyme which may be referred to as C4C3F5-H appears to be a broad spectrum hydroxylase in the phenylproponoid pathway in plants FIG. 5 (SEQ ID 3 and 4) illustrates the P450-2 sequence.

EXAMPLE 5

Identifying Gymnosperm Promoter Regions

In order to identify gymnosperm promoter regions, sequences from loblolly pine PAL and 4CLlB and 4CL3B lignin genes were used as primers to screen the loblolly pine genomic library, using the GenomeWalker Kit. The loblolly pine PAL primer sequence was obtained from the GenBank, reference number U39792. The loblolly pine 4CL1B primer sequences were also obtained from the gene bank, reference numbers U39404 and U39405.

The loblolly pine genomic library was constructed in Lambda DashII, available from Stratagene, of LaJolla, Calif. $3 \times 10^6$ phage plaques from the genomic library of loblolly pine were screened using both the above mentioned PAL cDNA and 4CL (PCR clone) fragments as probes. Five 4CL clones were obtained after screening. Lambda DNAs of two 4CL of the five 4CL clones obtained after screening were isolated and digested by EcoRV, Pstd, SalI and XbaI for Southern analysis. Southern analysis using 4CL fragments as probes indicated that both clones for the 4CL gene were identical. Results from further mapping showed that none of the original five 4CL clones contained promoter regions. When tested, the PAL clones obtained from the screening also did not contain promoter regions.

In a second attempt to clone the promoter regions associated with the PAL and 4CL a Universal GenomeWalker (TM) kit, available from Clontech, was used. In the process, total DNA from loblolly pine was digested by several restriction enzymes and ligated into the adaptors (libraries) provided with the kit. Two gene-specific primers for each gene were designed (GSP1 and 2). After two rounds of PCR using these primers and adapter primers of the kit, several fragments were amplified from each library. A 1.6 kb fragment and a 0.6 kb fragment for PAL gene and a 2.3 kb fragment (4CL1B) and a 0.7 kb fragment (4CL3B) for the 4CL gene were cloned, sequenced and found to contain promoter regions for all three genes. See FIG. 6 (SEQ ID 10), 7 (SEQ ID 11) and 8 (SEQ ID 9).

EXAMPLE 6

Fusing the ASL DNA Sequence to A Constitutive Promoter Region and Inserting the Expression Cassette Into a Gymnosperm Genome As a first step, a ASL DNA sequence, P450-1, was fused with a constitutive promoter region according to the methods described in the above Section IV to form an P450-1 expression cassette. A second ASL DNA sequence, P450-2, was then fused with a constitutive promoter in the same manner to form an P450-2 expression cassette. The P450-1 expression cassette was inserted into the gymnosperm genome by micro-projectile bombardment. Embryogenic tissue cultures of loblolly pine were initiated from immature zygotic embryos. The tissue was maintained in an undifferentiated state on semi-solid proliferation medium, according to methods described by Newton et al. TAES Technical Publication "Somatic Embryogenesis in Slash Pine", 1995 and Keinonen-Mettala et al. 1996, Scand. J. For. Res. 11: 242–250.

After separation, 5 ml of the liquid cell suspension fraction which passes through the 40 mesh screen was vacuum deposited onto filter paper and placed on semi-solid proliferation medium. The prepared gymnosperm target cells were then grown for 2 days on filter paper discs placed on semi-solid proliferation medium in a petri dish. These target cells were then bombarded with plasmnid DNA containing the P450-1 expression cassette and an expression cassette containing a selectable marker gene encoding the enzyme which confers resistance to the antibiotic hygromycin B. A 1:1 mixture of of selectable marker expression cassette and plasmid DNA containing the P450-1 expression cassette is precipitated with gold (1.5–3.0 microns) as described by Sanford et al. (1992). The DNA-coated microprojectiles were rinsed in absolute ethanol and aliquots of 10 $\mu l$ (5 $\mu g$ DNA/3 mg gold) were dried onto a macrocarrier, such as those available from BioRad (Hercules, Calif.).

Prior to bombardment, embryogenic tissue was desiccated under a sterile laminar-flow hood for 5 minutes. The desiccated tissue was transferred to semi-solid proliferation medium. The microprojectiles were accelerated into desiccated target cells using a BioRad PDS-1000/HE particle gun.

Each plate was bombarded once, rotated 180 degrees, and bombarded a second time. Preferred bombardment parameters were 1350 psi rupture disc pressure, 6 mm distance from the rupture disc to macrocarrier (gap distance), 1 cm macrocarrier travel distance, and 10 cm distance from macrocarrier stopping screen to culture plate (microcarrier travel distance). Tissue was then transferred to semi-solid proliferation medium containing hygromycin B for two days after bombardment.

The P450-2 expression cassette was inserted into the gymnosperm genome according to the same procedures.

EXAMPLE 7

Selecting Transformed Target Cells

After insertion of the P450-2 expression cassette and the selectable marker expression cassette into the gymnosperm target cells as described in Example 6, transformed cells were selected by exposure to an antibiotic that causes mortality of any cells not containing the GSL expression cassette. Forty independent cell lines were established from cultures co-bombarded with an expression cassette containing a hygromycin resistance gene construct and the P450-1 construct. These cell lines include lines Y2, Y17, Y7 and O4, as discussed in more detail below.

PCR techniques were then used to verify that the P450-1 gene had been successfully integrated into the genomes of the established cell lines by extracting genomic DNA using the Plant DNAeasy kit, available from Qiagen. 200 ng DNA from each cell line were used for each PCR reaction. Two P450-1 specific primers were designed to perform a PCR reaction with a 600 bp PCR product size. The primers were:

LsP450-iml-S primer: ATGGCTTTCCTTCTAATAC-CCATCTC (SEQ ID 23), and

LsP450-iml-A primer: GGGTGTAATGGACGAG-CAAGGACTTG (SEQ ID 24).

Each PCR reaction (100 μl) consisted of 75 μl $H_2O$, 1 μl $MgCl_2$ (25 mM), 10 μl PCR buffer 1 μl 10 mM dNTPs, and 10 μl DNA. 100 μl oil was layered on the top of each reaction mix. Hot start PCR was done as follows: PCR reaction was incubated at 95 degrees C. for 7 minutes and 1 μl each of both LsP450-iml-S and LsP450-iml-A primers (100 μM stock) and 1 μl of Taq polymerase were added through oil in each reaction. The PCR program used was 95 degrees C. for 1.5 minutes, 55 degrees C. for 45 seconds and 72 degrees C. for 2 minutes, repeated for 40 cycles, followed by extension at 72 degrees C. for 10 minutes.

The above PCR products were employed to determine if gymnosperm cells contained the angiosperm lignin gene sequences. With reference to FIG. 9, PCR amplification was performed using template DNA from cells which grew vigorously on hygromycin B-containing medium. The PCR products were electrophoresed in an agarose gel containing 9 lanes. Lanes 1–4 contained PCR amplification of products of the Sweetgum P450-1 gene from a non-transformed control and transgenic loblolly pine cell lines. Lane 1 contained the non-transformed control PT52. Lane 2 contained transgenic line Y2. Lane 3 contained transgenic line Y17 and Lane 4 contained the plasmid which contains the expression cassette PpSLsP450-im-S. Lanes 2 through 4 all contain an amplified fragment of about 600 bp, indicating that the P450-1 gene has been successfully inserted into transgenic cell lines Y2 and Y17.

Lane 5 contained a DNA size marker Phi 174/HaeII (BRL). The top four bands in this lane indicate molecular sizes of 1353, 1078, 872 and 603 bp.

Lanes 6–9 contained PCR amplification products of hygromycin B gene from non-transformed control and transgenic loblolly pine cell lines. Lane 6 contained the non-transformed control lane referenced to as PTS. Lane 7 contained transgenic line Y7. Lane 8 contained transgenic line O4. Lane 9 contained the plasmid which includes the expression cassette containing the gene encoding the enzyme which confers resistance to the antibiotic hygromycin B. Lanes 7–9 all show an amplified fragment of about 1000 bp, indicating that the hygromycin gene has been successfully inserted into transgenic lines Y7 and O4.

These PCR results confirmed the presence of P450-1 and hygromycin resistance gene in transformed loblolly pine cell cultures. The results obtained from the PCR verification of 4 cell lines, and similar tests with the remaining 36 cell lines, confirm stable integration of the P450-1 gene and the hygromycin B gene in 25% of the 40 cell lines.

In addition, loblolly pine embryogenic cells which have been co-bombarded with the P450-2 and hygromycin B expression cassettes, are growing vigorously on hygromycin selection medium, indicating that the P450-2 expression cassette was successfully integrated into the gymnosperm genome.

Although various embodiments and features of the invention have been described in the foregoing detailed description, those of ordinary skill will recognize the invention is capable of numerous modifications, rearrangements and substitutions without departing from the scope of the invention as set forth in the appended claims. For example, in the case where the lignin DNA sequence is transcribed and translated to produce a functional syringyl lignin gene, those of ordinary skill will recognize that because of codon degeneracy a number of polynucleotide sequences will encode the same gene. These variants are intended to be covered by the DNA sequences disclosed and claimed herein. In addition, the sequences claimed herein include those sequences with encode a gene having substantial functional identity with those claimed. Thus, in the case of syringyl lignin genes, for example, the DNA sequences include variant polynucleotide sequences encoding polypeptides which have substantial identity with the amino acid sequence of syringyl lignin and which show syringyl lignin activity in gymnosperms.

What is claimed is:

1. An isolated P450-2DNA sequence which encodes an enzyme involved in the biosynthesis of syringyl lignin monomer units, wherein said DNA is as shown in SEQ ID No. 3 and said DNA encodes SEQ ID No. 4.

2. A method for modifying the genome of loblolly pine which comprises cloning the sweetgum P450-2 polynucleotide, fusing it to a constitutive promoter to form an expresion cassette, and inserting the expression cassette into the loblolly pine genome.

3. A loblolly pine containing the sweetgum P450-2 polynucleotide.

4. A method for modifying the genome of a gymnosperm which comprises cloning the sweetgum P450-2polynucleotide, fusing it to a constutitve promoter to or an expression cassette, and inserting the expression cassette into a gymnosperm genome.

5. A gymnosperm plant containing the sweetgum P450-2 polynucleotide.

6. A gymnosperm plant containing a DNA molecule selected from the group consisting of the DNA sequence of SEQ ID No. 3 and a DNA sequence that encodes SEQ ID No. 4.

7. The gymnosperm plant of claim 5, further comprising syringyl lignin.

* * * * *

UNITED STATES PATENT AND TRADEMARK OFFICE
CERTIFICATE OF CORRECTION

PATENT NO. : 6,252,135 B1
DATED : June 26, 2001
INVENTOR(S) : Vincent L. Chiang et al.

It is certified that error appears in the above-identified patent and that said Letters Patent is hereby corrected as shown below:

Column 1,
Line 10, delete "contaniing" and insert -- containing --.

Column 2,
Line 12, delete "acheived" and insert -- achieved --.

Column 3,
Line 27, delete "ferulic-5-hydroxylase (P450-1)... (SEQ ID1) and insert -- P450-1... (SEQ ID 1 and 2) --.

Column 4,
Line 11, delete "MnRNA" and insert -- mRNA --.
Line 37, delete "ligin" and insert -- lignin --.

Column 5,
Line 23, delete "P450like" and insert -- P450-like --.
Line 27, delete "xylme" and insert -- xylem --.
Line 28, delete "disignated" and insert -- designated --.
Line 42, delete "beleived" and insert -- believed --.

Column 8,
Line 48, delete "acheive" and insert -- achieve --.

Column 9,
Line 30, delete "bi OMT" and insert -- bi-OMT --.
Line 49, delete "Thlr ...lie" and insert -- Thr...Ile --
Line 50, delete "lie ... lie ... lie ... lie" and insert -- Ile ... Ile ... Ile ... Ile --.
Line 51, delete "Mrg" and insert -- Arg --.
Line 52, delete "Hie" and insert -- Ile --.
Line 53, delete "ile ... lie ... Mg ... Mig ... fle" and insert -- Ile ... Ile ... Arg ... Arg ... Ile --.
Line 55, delete "HIS" and insert -- H1S --.
Line 57, delete "Hie ...Mrg" and insert -- Ile ...Arg --.
Line 58, delete "lie ...Thlr" and insert -- Ile ...Thr --.

UNITED STATES PATENT AND TRADEMARK OFFICE
CERTIFICATE OF CORRECTION

PATENT NO. : 6,252,135 B1
DATED : June 26, 2001
INVENTOR(S) : Vincent L. Chiang et al.

It is certified that error appears in the above-identified patent and that said Letters Patent is hereby corrected as shown below:

Column 11,
Line 7, "TTTTTTTTTT" and insert -- TTTTTTTTTTT --.
Line 8, "TTTTTTTTTT" and insert -- TTTTTTTTTTT --.
Line 59, delete "mg" and insert -- µg --.

Column 12,
Line 11, delete "A12-3'" and insert -- Arg-3' --.

Column 13,
Line 5, delete "FSH" and insert -- F5H --.
Line 7, delete "P450-2" and insert -- FA5H-2 --.
Line 29, delete "prtoein" and insert -- protein --.
Line 30, delete "proten" and insert -- protein --.
Line 55, delete "Pstd, SalI" and insert -- PsI, SalI --.

Column 14,
Line 36, delete "plasmnid" and insert -- plasmid --.
Line 40, delete "of of" and insert -- of --.

Column 15,
Line 44, delete "PpSLsP450-im-S" and insert -- pSSLsP450-1-im-s --.

Column 16,
Line 1, delete "174/HaeII" and insert -- 174/HaeIII --.
Line 7, delete "control lane ... PTS" and insert -- control line ... PT52 --.

UNITED STATES PATENT AND TRADEMARK OFFICE
CERTIFICATE OF CORRECTION

PATENT NO. : 6,252,135 B1
DATED : June 26, 2001
INVENTOR(S) : Vincent L. Chiang et al.

It is certified that error appears in the above-identified patent and that said Letters Patent is hereby corrected as shown below:

<u>Column 50,</u>
Line 49, delete "or" and insert -- form --.

Signed and Sealed this

Twelfth Day of March, 2002

Attest:

Attesting Officer

JAMES E. ROGAN
*Director of the United States Patent and Trademark Office*

SEQUENCE LISTING

```
<160> NUMBER OF SEQ ID NOS:  24

<210> SEQ ID NO 1
<211> LENGTH: 1708
<212> TYPE: DNA
<213> ORGANISM: Liquidambar styraciflua
<220> FEATURE:
<221> NAME/KEY: CDS
<222> LOCATION: (48)..(1571)

<400> SEQUENCE: 1
cggcacgagg aaaccctaaa actcacctct cttacccttt ctcttca atg gct ttc         56
                                                    Met Ala Phe
                                                      1 ctt cta ata ccc atc tca ata atc ttc atc gtc tta gct tac cag ctc        104
```

-continued

```
Leu Leu Ile Pro Ile Ser Ile Ile Phe Ile Val Leu Ala Tyr Gln Leu
 5                  10                  15 tat caa cgg ctc aga ttt aag ctc cca ccc ggc cca cgt cca tgg ccg       152
Tyr Gln Arg Leu Arg Phe Lys Leu Pro Pro Gly Pro Arg Pro Trp Pro
 20              25                  30                  35 atc gtc gga aac ctt tac gac ata aaa ccg gtg agg ttc cgg tgt ttc       200
Ile Val Gly Asn Leu Tyr Asp Ile Lys Pro Val Arg Phe Arg Cys Phe
                 40                  45                  50 gcc gag tgg tca caa gcg tac ggt ccg atc ata tcg gtg tgg ttc ggt       248
Ala Glu Trp Ser Gln Ala Tyr Gly Pro Ile Ile Ser Val Trp Phe Gly
             55                  60                  65 tca acg ttg aat gtg atc gta tcg aat tcg gaa ttg gct aag gaa gtg       296
Ser Thr Leu Asn Val Ile Val Ser Asn Ser Glu Leu Ala Lys Glu Val
         70                  75                  80 ctc aag gaa aaa gat caa caa ttg gct gat agg cat agg agt aga tca       344
Leu Lys Glu Lys Asp Gln Gln Leu Ala Asp Arg His Arg Ser Arg Ser
 85                  90                  95 gct gcc aaa ttt agc agg gat ggg cag gac ctt ata tgg gct gat tat       392
Ala Ala Lys Phe Ser Arg Asp Gly Gln Asp Leu Ile Trp Ala Asp Tyr
100             105                 110                 115 gga cct cac tat gtg aag gtt aca aag gtt tgt acc ctc gag ctt ttt       440
Gly Pro His Tyr Val Lys Val Thr Lys Val Cys Thr Leu Glu Leu Phe
                120                 125                 130 act cca aag cgg ctt gaa gct ctt aga ccc att aga gaa gat gaa gtt       488
Thr Pro Lys Arg Leu Glu Ala Leu Arg Pro Ile Arg Glu Asp Glu Val
            135                 140                 145 aca gcc atg gtt gag tcc att ttt aat gac act gcg aat cct gaa aat       536
Thr Ala Met Val Glu Ser Ile Phe Asn Asp Thr Ala Asn Pro Glu Asn
        150                 155                 160 tat ggg aag agt atg ctg gtg aag aag tat ttg gga gca gta gca ttc       584
Tyr Gly Lys Ser Met Leu Val Lys Lys Tyr Leu Gly Ala Val Ala Phe
    165                 170                 175 aac aac att aca aga ctc gca ttt gga aag cga ttc gtg aat tca gag       632
Asn Asn Ile Thr Arg Leu Ala Phe Gly Lys Arg Phe Val Asn Ser Glu
180                 185                 190                 195 ggt gta atg gac gag caa gga ctt gaa ttt aag gaa att gtg gcc aat       680
Gly Val Met Asp Glu Gln Gly Leu Glu Phe Lys Glu Ile Val Ala Asn
                200                 205                 210 gga ctc aag ctt ggt gcc tca ctt gca atg gct gag cac att cct tgg       728
Gly Leu Lys Leu Gly Ala Ser Leu Ala Met Ala Glu His Ile Pro Trp
            215                 220                 225 ctc cgt tgg atg ttc cca ctt gag gaa ggg gcc ttt gcc aag cat ggg       776
Leu Arg Trp Met Phe Pro Leu Glu Glu Gly Ala Phe Ala Lys His Gly
        230                 235                 240 gca cgt agg gac cga ctt acc aga gct atc atg gaa gag cac aca ata       824
Ala Arg Arg Asp Arg Leu Thr Arg Ala Ile Met Glu Glu His Thr Ile
    245                 250                 255 gcc cgt aaa aag agt ggt gga gcc caa caa cat ttc gtg gat gca ttg       872
Ala Arg Lys Lys Ser Gly Gly Ala Gln Gln His Phe Val Asp Ala Leu
260                 265                 270                 275 ctc acc cta caa gag aaa tat gac ctt agc gag gac act att att ggg       920
Leu Thr Leu Gln Glu Lys Tyr Asp Leu Ser Glu Asp Thr Ile Ile Gly
                280                 285                 290 ctc ctt tgg gat atg atc act gca ggc atg gac aca acc gca atc tct       968
Leu Leu Trp Asp Met Ile Thr Ala Gly Met Asp Thr Thr Ala Ile Ser
            295                 300                 305 gtc gaa tgg gcc atg gcc gag tta att aag aac cca agg gtg caa caa      1016
Val Glu Trp Ala Met Ala Glu Leu Ile Lys Asn Pro Arg Val Gln Gln
        310                 315                 320
```

```
aaa gct caa gag gag cta gac aat gta ctt ggg tcc gaa cgt gtc ctg      1064
Lys Ala Gln Glu Glu Leu Asp Asn Val Leu Gly Ser Glu Arg Val Leu
325                 330                 335 acc gaa ttg gac ttc tca agc ctc cct tat cta caa tgt gta gcc aag      1112
Thr Glu Leu Asp Phe Ser Ser Leu Pro Tyr Leu Gln Cys Val Ala Lys
340                 345                 350                 355 gag gca cta agg ctg cac cct cca aca cca cta atg ctc cct cat cgc      1160
Glu Ala Leu Arg Leu His Pro Pro Thr Pro Leu Met Leu Pro His Arg
                360                 365                 370 gcc aat gcc aac gtc aaa att ggt ggc tac gac atc cct aag gga tca      1208
Ala Asn Ala Asn Val Lys Ile Gly Gly Tyr Asp Ile Pro Lys Gly Ser
            375                 380                 385 aat gtt cat gta aat gtc tgg gcc gtg gct cgt gat cca gca gtg tgg      1256
Asn Val His Val Asn Val Trp Ala Val Ala Arg Asp Pro Ala Val Trp
        390                 395                 400 cgt gac cca cta gag ttt cga ccg gaa cgg ttc tct gaa gac gat gtc      1304
Arg Asp Pro Leu Glu Phe Arg Pro Glu Arg Phe Ser Glu Asp Asp Val
    405                 410                 415 gac atg aaa ggt cac gat tat agg cta ctg ccg ttt ggt gca ggg agg      1352
Asp Met Lys Gly His Asp Tyr Arg Leu Leu Pro Phe Gly Ala Gly Arg
420                 425                 430                 435 cgt gtt tgc ccc ggt gca caa ctt ggc atc aat ttg gtc aca tcc atg      1400
Arg Val Cys Pro Gly Ala Gln Leu Gly Ile Asn Leu Val Thr Ser Met
                440                 445                 450 atg ggt cac cta ttg cac cat ttc tat tgg agc cct cct aaa ggt gta      1448
Met Gly His Leu Leu His His Phe Tyr Trp Ser Pro Pro Lys Gly Val
            455                 460                 465 aaa cca gag gag att gac atg tca gag aat cca gga ttg gtc acc tac      1496
Lys Pro Glu Glu Ile Asp Met Ser Glu Asn Pro Gly Leu Val Thr Tyr
        470                 475                 480 atg cga acc ccg gtg caa gct gtt ccc act cca agg ctg cct gct cac      1544
Met Arg Thr Pro Val Gln Ala Val Pro Thr Pro Arg Leu Pro Ala His
    485                 490                 495 ttg tac aaa cgt gta gct gtg gat atg taattcttag tttgttatta            1591
Leu Tyr Lys Arg Val Ala Val Asp Met
500                 505 ttcatgctct taaggttttg gactttgaac ttatgatgag atttgtaaaa ttccaagtga    1651
tcaaatgaag aaaagaccaa ataaaaaggc ttgacgattt aaaaaaaaaa aaaaaaa       1708

<210> SEQ ID NO 2
<211> LENGTH: 508
<212> TYPE: PRT
<213> ORGANISM: Liquidambar styraciflua

<400> SEQUENCE: 2

Met Ala Phe Leu Leu Ile Pro Ile Ser Ile Ile Phe Ile Val Leu Ala
1               5                   10                  15

Tyr Gln Leu Tyr Gln Arg Leu Arg Phe Lys Leu Pro Pro Gly Pro Arg
            20                  25                  30

Pro Trp Pro Ile Val Gly Asn Leu Tyr Asp Ile Lys Pro Val Arg Phe
        35                  40                  45

Arg Cys Phe Ala Glu Trp Ser Gln Ala Tyr Gly Pro Ile Ile Ser Val
    50                  55                  60

Trp Phe Gly Ser Thr Leu Asn Val Ile Val Ser Asn Ser Glu Leu Ala
65                  70                  75                  80

Lys Glu Val Leu Lys Glu Lys Asp Gln Gln Leu Ala Asp Arg His Arg
                85                  90                  95

Ser Arg Ser Ala Ala Lys Phe Ser Arg Asp Gly Gln Asp Leu Ile Trp
```

```
                    100                 105                 110
Ala Asp Tyr Gly Pro His Tyr Val Lys Val Thr Lys Val Cys Thr Leu
            115                 120                 125

Glu Leu Phe Thr Pro Lys Arg Leu Glu Ala Leu Arg Pro Ile Arg Glu
    130                 135                 140

Asp Glu Val Thr Ala Met Val Glu Ser Ile Phe Asn Asp Thr Ala Asn
145                 150                 155                 160

Pro Glu Asn Tyr Gly Lys Ser Met Leu Val Lys Lys Tyr Leu Gly Ala
                165                 170                 175

Val Ala Phe Asn Asn Ile Thr Arg Leu Ala Phe Gly Lys Arg Phe Val
            180                 185                 190

Asn Ser Glu Gly Val Met Asp Glu Gln Gly Leu Glu Phe Lys Glu Ile
    195                 200                 205

Val Ala Asn Gly Leu Lys Leu Gly Ala Ser Leu Ala Met Ala Glu His
210                 215                 220

Ile Pro Trp Leu Arg Trp Met Phe Pro Leu Glu Gly Ala Phe Ala
225                 230                 235                 240

Lys His Gly Ala Arg Arg Asp Arg Leu Thr Arg Ala Ile Met Glu Glu
                245                 250                 255

His Thr Ile Ala Arg Lys Ser Gly Gly Ala Gln Gln His Phe Val
            260                 265                 270

Asp Ala Leu Leu Thr Leu Gln Glu Lys Tyr Asp Leu Ser Glu Asp Thr
    275                 280                 285

Ile Ile Gly Leu Leu Trp Asp Met Ile Thr Ala Gly Met Asp Thr Thr
290                 295                 300

Ala Ile Ser Val Glu Trp Ala Met Ala Glu Leu Ile Lys Asn Pro Arg
305                 310                 315                 320

Val Gln Gln Lys Ala Gln Glu Glu Leu Asp Asn Val Leu Gly Ser Glu
                325                 330                 335

Arg Val Leu Thr Glu Leu Asp Phe Ser Ser Leu Pro Tyr Leu Gln Cys
            340                 345                 350

Val Ala Lys Glu Ala Leu Arg Leu His Pro Pro Thr Pro Leu Met Leu
    355                 360                 365

Pro His Arg Ala Asn Ala Asn Val Lys Ile Gly Gly Tyr Asp Ile Pro
370                 375                 380

Lys Gly Ser Asn Val His Val Asn Val Trp Ala Val Ala Arg Asp Pro
385                 390                 395                 400

Ala Val Trp Arg Asp Pro Leu Glu Phe Arg Pro Glu Arg Phe Ser Glu
                405                 410                 415

Asp Asp Val Asp Met Lys Gly His Asp Tyr Arg Leu Leu Pro Phe Gly
            420                 425                 430

Ala Gly Arg Arg Val Cys Pro Gly Ala Gln Leu Gly Ile Asn Leu Val
    435                 440                 445

Thr Ser Met Met Gly His Leu Leu His His Phe Tyr Trp Ser Pro Pro
450                 455                 460

Lys Gly Val Lys Pro Glu Glu Ile Asp Met Ser Glu Asn Pro Gly Leu
465                 470                 475                 480

Val Thr Tyr Met Arg Thr Pro Val Gln Ala Val Pro Thr Pro Arg Leu
                485                 490                 495

Pro Ala His Leu Tyr Lys Arg Val Ala Val Asp Met
            500                 505

<210> SEQ ID NO 3
```

-continued

```
<211> LENGTH: 1883
<212> TYPE: DNA
<213> ORGANISM: Liquidambar styraciflua
<220> FEATURE:
<221> NAME/KEY: CDS
<222> LOCATION: (74)..(1606)

<400> SEQUENCE: 3
```

| | |
|---|---:|
| tgcaaacctg cacaaacaaa gagagagaag aagaaaaagg aagagaggag agagagagag | 60 |
| agagagagaa gcc atg gat tct tct ctt cat gaa gcc ttg caa cca cta<br>                Met Asp Ser Ser Leu His Glu Ala Leu Gln Pro Leu<br>                 1               5              10 | 109 |
| ccc atg acg ctg ttc ttc att ata cct ttg cta ctc tta ttg ggc cta<br>Pro Met Thr Leu Phe Phe Ile Ile Pro Leu Leu Leu Leu Leu Gly Leu<br>         15                 20                 25 | 157 |
| gta tct cgg ctt cgc cag aga cta cca tac cca cca ggc cca aaa ggc<br>Val Ser Arg Leu Arg Gln Arg Leu Pro Tyr Pro Pro Gly Pro Lys Gly<br> 30                 35                 40 | 205 |
| tta ccg gtg atc gga aac atg ctc atg atg gat caa ctc act cac cga<br>Leu Pro Val Ile Gly Asn Met Leu Met Met Asp Gln Leu Thr His Arg<br> 45                 50               55              60 | 253 |
| gga ctc gcc aaa ctc gcc aaa caa tac ggc ggt cta ttc cac ctc aag<br>Gly Leu Ala Lys Leu Ala Lys Gln Tyr Gly Gly Leu Phe His Leu Lys<br>               65                 70               75 | 301 |
| atg gga ttc tta cac atg gtg gcc gtt tcc aca ccc gac atg gct cgc<br>Met Gly Phe Leu His Met Val Ala Val Ser Thr Pro Asp Met Ala Arg<br>               80                 85               90 | 349 |
| caa gtc ctt caa gtc caa gac aac atc ttc tcg aac cgg cca gcc acc<br>Gln Val Leu Gln Val Gln Asp Asn Ile Phe Ser Asn Arg Pro Ala Thr<br>               95                100             105 | 397 |
| ata gcc atc agc tac ctc acc tat gac cga gcc gac atg gcc ttc gct<br>Ile Ala Ile Ser Tyr Leu Thr Tyr Asp Arg Ala Asp Met Ala Phe Ala<br>110                115                120 | 445 |
| cac tac ggc ccg ttt tgg cgt cag atg cgt aaa ctc tgc gtc atg aaa<br>His Tyr Gly Pro Phe Trp Arg Gln Met Arg Lys Leu Cys Val Met Lys<br>125                130               135             140 | 493 |
| tta ttt agc cgg aaa cga gcc gag tcg tgg gag tcg gtc cga gac gag<br>Leu Phe Ser Arg Lys Arg Ala Glu Ser Trp Glu Ser Val Arg Asp Glu<br>               145                150              155 | 541 |
| gtc gac tcg gca gta cga gtg gtc gcg tcc aat att ggg tcg acg gtg<br>Val Asp Ser Ala Val Arg Val Val Ala Ser Asn Ile Gly Ser Thr Val<br>            160                165              170 | 589 |
| aat atc ggc gag ctg gtt ttt gct ctg acg aag aat att act tac agg<br>Asn Ile Gly Glu Leu Val Phe Ala Leu Thr Lys Asn Ile Thr Tyr Arg<br>           175                180              185 | 637 |
| gcg gct ttt ggg acg atc tcg cat gag gac cag gac gag ttc gtg gcc<br>Ala Ala Phe Gly Thr Ile Ser His Glu Asp Gln Asp Glu Phe Val Ala<br>      190                195              200 | 685 |
| ata ctg caa gag ttt tcg cag ctg ttt ggt gct ttt aat ata gct gat<br>Ile Leu Gln Glu Phe Ser Gln Leu Phe Gly Ala Phe Asn Ile Ala Asp<br>205                210               215             220 | 733 |
| ttt atc cct tgg ctc aaa tgg gtt cct cag ggg att aac gtc agg ctc<br>Phe Ile Pro Trp Leu Lys Trp Val Pro Gln Gly Ile Asn Val Arg Leu<br>               225                230              235 | 781 |
| aac aag gca cga ggg gcg ctt gat ggg ttt att gac aag atc atc gac<br>Asn Lys Ala Arg Gly Ala Leu Asp Gly Phe Ile Asp Lys Ile Ile Asp<br>            240                245              250 | 829 |
| gat cat ata cag aag ggg agt aaa aac tcg gag gag gtt gat act gat<br>Asp His Ile Gln Lys Gly Ser Lys Asn Ser Glu Glu Val Asp Thr Asp<br>           255                260              265 | 877 |

```
atg gta gat gat tta ctt gct ttt tac ggt gag gaa gcc aaa gta agc    925
Met Val Asp Asp Leu Leu Ala Phe Tyr Gly Glu Glu Ala Lys Val Ser
    270                 275                 280 gaa tct gac gat ctt caa aat tcc atc aaa ctc acc aaa gac aac atc    973
Glu Ser Asp Asp Leu Gln Asn Ser Ile Lys Leu Thr Lys Asp Asn Ile
285                 290                 295                 300 aaa gct atc atg gac gta atg ttt gga ggg acc gaa acg gtg gcg tcc   1021
Lys Ala Ile Met Asp Val Met Phe Gly Gly Thr Glu Thr Val Ala Ser
                305                 310                 315 gcg att gaa tgg gcc atg acg gag ctg atg aaa agc cca gaa gat cta   1069
Ala Ile Glu Trp Ala Met Thr Glu Leu Met Lys Ser Pro Glu Asp Leu
            320                 325                 330 aag aag gtc caa caa gaa ctc gcc gtg gtg gtg ggt ctt gac cgg cga   1117
Lys Lys Val Gln Gln Glu Leu Ala Val Val Val Gly Leu Asp Arg Arg
        335                 340                 345 gtc gaa gag aaa gac ttc gag aag ctc acc tac ttg aaa tgc gta ctg   1165
Val Glu Glu Lys Asp Phe Glu Lys Leu Thr Tyr Leu Lys Cys Val Leu
    350                 355                 360 aag gaa gtc ctt cgc ctc cac cca ccc atc cca ctc ctc ctc cac gag   1213
Lys Glu Val Leu Arg Leu His Pro Pro Ile Pro Leu Leu Leu His Glu
365                 370                 375                 380 act gcc gag gac gcc gag gtc ggc ggc tac tac att ccg gcg aaa tcg   1261
Thr Ala Glu Asp Ala Glu Val Gly Gly Tyr Tyr Ile Pro Ala Lys Ser
                385                 390                 395 cgg gtg atg atc aac gcg tgc gcc atc ggc cgg gac aag aac tcg tgg   1309
Arg Val Met Ile Asn Ala Cys Ala Ile Gly Arg Asp Lys Asn Ser Trp
            400                 405                 410 gcc gac cca gat acg ttt agg ccc tcc agg ttt ctc aaa gac ggt gtg   1357
Ala Asp Pro Asp Thr Phe Arg Pro Ser Arg Phe Leu Lys Asp Gly Val
        415                 420                 425 ccc gat ttc aaa ggg aac aac ttc gag ttc atc cca ttc ggg tca ggt   1405
Pro Asp Phe Lys Gly Asn Asn Phe Glu Phe Ile Pro Phe Gly Ser Gly
    430                 435                 440 cgt cgg tct tgc ccc ggt atg caa ctc gga ctc tac gcg cta gag acg   1453
Arg Arg Ser Cys Pro Gly Met Gln Leu Gly Leu Tyr Ala Leu Glu Thr
445                 450                 455                 460 act gtg gct cac ctc ctt cac tgt ttc acg tgg gag ttg ccg gac ggg   1501
Thr Val Ala His Leu Leu His Cys Phe Thr Trp Glu Leu Pro Asp Gly
                465                 470                 475 atg aaa ccg agt gaa ctc gag atg aat gat gtg ttt gga ctc acc gcg   1549
Met Lys Pro Ser Glu Leu Glu Met Asn Asp Val Phe Gly Leu Thr Ala
            480                 485                 490 cca aga gcg att cga ctc acc gcc gtg ccg agt cca cgc ctt ctc tgt   1597
Pro Arg Ala Ile Arg Leu Thr Ala Val Pro Ser Pro Arg Leu Leu Cys
        495                 500                 505 cct ctc tat tgatcgaatg attgggggag ctttgtggag gggcttttat           1646
Pro Leu Tyr
    510 ggagactcta tatatagatg ggaagtgaaa caacgacagg tgaatgcttg gattttggt   1706 atatattggg gagggagggg aaaaaaaaaa taatgaaagg aaagaaaaga gagaatttga  1766 atttctcttc ctctgtggat aaaagcctcg ttttttaattg tttttatgtg gagatatttg  1826 tgtttgttta tttttatctc tttttttgca ataacactca aaaataaaaa aaaaaaa     1883
```

<210> SEQ ID NO 4
<211> LENGTH: 511
<212> TYPE: PRT
<213> ORGANISM: Liquidambar styraciflua

<400> SEQUENCE: 4

```
Met Asp Ser Ser Leu His Glu Ala Leu Gln Pro Leu Pro Met Thr Leu
 1               5                  10                  15

Phe Phe Ile Ile Pro Leu Leu Leu Leu Gly Leu Val Ser Arg Leu
            20                  25                  30

Arg Gln Arg Leu Pro Tyr Pro Gly Pro Lys Gly Leu Pro Val Ile
        35                  40                  45

Gly Asn Met Leu Met Met Asp Gln Leu Thr His Arg Gly Leu Ala Lys
        50                  55                  60

Leu Ala Lys Gln Tyr Gly Gly Leu Phe His Leu Lys Met Gly Phe Leu
65                  70                  75                  80

His Met Val Ala Val Ser Thr Pro Asp Met Ala Arg Gln Val Leu Gln
                85                  90                  95

Val Gln Asp Asn Ile Phe Ser Asn Arg Pro Ala Thr Ile Ala Ile Ser
                100                 105                 110

Tyr Leu Thr Tyr Asp Arg Ala Asp Met Ala Phe Ala His Tyr Gly Pro
        115                 120                 125

Phe Trp Arg Gln Met Arg Lys Leu Cys Val Met Lys Leu Phe Ser Arg
        130                 135                 140

Lys Arg Ala Glu Ser Trp Glu Ser Val Arg Asp Glu Val Asp Ser Ala
145                 150                 155                 160

Val Arg Val Val Ala Ser Asn Ile Gly Ser Thr Val Asn Ile Gly Glu
                165                 170                 175

Leu Val Phe Ala Leu Thr Lys Asn Ile Thr Tyr Arg Ala Ala Phe Gly
            180                 185                 190

Thr Ile Ser His Glu Asp Gln Asp Glu Phe Val Ala Ile Leu Gln Glu
        195                 200                 205

Phe Ser Gln Leu Phe Gly Ala Phe Asn Ile Ala Asp Phe Ile Pro Trp
    210                 215                 220

Leu Lys Trp Val Pro Gln Gly Ile Asn Val Arg Leu Asn Lys Ala Arg
225                 230                 235                 240

Gly Ala Leu Asp Gly Phe Ile Asp Lys Ile Ile Asp Asp His Ile Gln
                245                 250                 255

Lys Gly Ser Lys Asn Ser Glu Glu Val Asp Thr Asp Met Val Asp Asp
            260                 265                 270

Leu Leu Ala Phe Tyr Gly Glu Glu Ala Lys Val Ser Glu Ser Asp Asp
        275                 280                 285

Leu Gln Asn Ser Ile Lys Leu Thr Lys Asp Asn Ile Lys Ala Ile Met
        290                 295                 300

Asp Val Met Phe Gly Gly Thr Glu Thr Val Ala Ser Ala Ile Glu Trp
305                 310                 315                 320

Ala Met Thr Glu Leu Met Lys Ser Pro Glu Asp Leu Lys Lys Val Gln
                325                 330                 335

Gln Glu Leu Ala Val Val Gly Leu Asp Arg Arg Val Glu Glu Lys
            340                 345                 350

Asp Phe Glu Lys Leu Thr Tyr Leu Lys Cys Val Leu Lys Glu Val Leu
        355                 360                 365

Arg Leu His Pro Pro Ile Pro Leu Leu His Glu Thr Ala Glu Asp
    370                 375                 380

Ala Glu Val Gly Gly Tyr Tyr Ile Pro Ala Lys Ser Arg Val Met Ile
385                 390                 395                 400

Asn Ala Cys Ala Ile Gly Arg Asp Lys Asn Ser Trp Ala Asp Pro Asp
            405                 410                 415
```

```
Thr Phe Arg Pro Ser Arg Phe Leu Lys Asp Gly Val Pro Asp Phe Lys
            420                 425                 430

Gly Asn Asn Phe Glu Phe Ile Pro Phe Gly Ser Gly Arg Arg Ser Cys
            435                 440                 445

Pro Gly Met Gln Leu Gly Leu Tyr Ala Leu Glu Thr Thr Val Ala His
        450                 455                 460

Leu Leu His Cys Phe Thr Trp Glu Leu Pro Asp Gly Met Lys Pro Ser
465                 470                 475                 480

Glu Leu Glu Met Asn Asp Val Phe Gly Leu Thr Ala Pro Arg Ala Ile
                485                 490                 495

Arg Leu Thr Ala Val Pro Ser Pro Arg Leu Leu Cys Pro Leu Tyr
            500                 505                 510

<210> SEQ ID NO 5
<211> LENGTH: 1380
<212> TYPE: DNA
<213> ORGANISM: Liquidambar styraciflua
<220> FEATURE:
<221> NAME/KEY: CDS
<222> LOCATION: (67)..(1170)

<400> SEQUENCE: 5
cggcacgagc cctacctcct ttcttggaaa aatttcccca ttcgatcaca atccgggcct      60 caaaaa atg gga tca aca agc gaa acg aag atg agc ccg agt gaa gca         108
       Met Gly Ser Thr Ser Glu Thr Lys Met Ser Pro Ser Glu Ala
         1               5                  10 gca gca gca gaa gaa gaa gca ttc gta ttc gct atg caa tta acc agt        156
Ala Ala Ala Glu Glu Glu Ala Phe Val Phe Ala Met Gln Leu Thr Ser
 15              20                  25                  30 gct tca gtt ctt ccc atg gtc cta aaa tca gcc ata gag ctc gac gtc        204
Ala Ser Val Leu Pro Met Val Leu Lys Ser Ala Ile Glu Leu Asp Val
                 35                  40                  45 tta gaa atc atg gct aaa gct ggt cca ggt gcg cac ata tcc aca tct        252
Leu Glu Ile Met Ala Lys Ala Gly Pro Gly Ala His Ile Ser Thr Ser
             50                  55                  60 gac ata gcc tct aag ctg ccc aca aag aat cca gat gca gcc gtc atg        300
Asp Ile Ala Ser Lys Leu Pro Thr Lys Asn Pro Asp Ala Ala Val Met
         65                  70                  75 ctt gac cgt atg ctc cgc ctc ttg gct agc tac tct gtt cta acg tgc        348
Leu Asp Arg Met Leu Arg Leu Leu Ala Ser Tyr Ser Val Leu Thr Cys
     80                  85                  90 tct ctc cgc acc ctc cct gac ggc aag atc gag agg ctt tac ggc ctt        396
Ser Leu Arg Thr Leu Pro Asp Gly Lys Ile Glu Arg Leu Tyr Gly Leu
 95                  100                 105                 110 gca ccc gtt tgt aaa ttc ttg acc aga aac gat gat gga gtc tcc ata        444
Ala Pro Val Cys Lys Phe Leu Thr Arg Asn Asp Asp Gly Val Ser Ile
                 115                 120                 125 gcc gct ctg tct ctc atg aat caa gac aag gtc ctc atg gag agc tgg        492
Ala Ala Leu Ser Leu Met Asn Gln Asp Lys Val Leu Met Glu Ser Trp
             130                 135                 140 tac cac ttg acc gag gca gtt ctt gaa ggt gga att cca ttt aac aag        540
Tyr His Leu Thr Glu Ala Val Leu Glu Gly Gly Ile Pro Phe Asn Lys
         145                 150                 155 gcc tat gga atg aca gca ttt gag tac cat ggc acc gat ccc aga ttc        588
Ala Tyr Gly Met Thr Ala Phe Glu Tyr His Gly Thr Asp Pro Arg Phe
     160                 165                 170 aac aca gtt ttc aac aat gga atg tcc aat cat tcg acc att acc atg        636
Asn Thr Val Phe Asn Asn Gly Met Ser Asn His Ser Thr Ile Thr Met
175                 180                 185                 190
```

```
aag aaa atc ctt gag act tac aaa ggg ttc gag gga ctt gga tct gtg      684
Lys Lys Ile Leu Glu Thr Tyr Lys Gly Phe Glu Gly Leu Gly Ser Val
                195                 200                 205 gtt gat gtt ggt ggt ggc act ggt gcc cac ctt aac atg att atc gct      732
Val Asp Val Gly Gly Gly Thr Gly Ala His Leu Asn Met Ile Ile Ala
            210                 215                 220 aaa tac ccc atg atc aag ggc att aac ttc gac ttg cct cat gtt att      780
Lys Tyr Pro Met Ile Lys Gly Ile Asn Phe Asp Leu Pro His Val Ile
        225                 230                 235 gag gag gct ccc tcc tat cct ggt gtg gag cat gtt ggt gga gat atg      828
Glu Glu Ala Pro Ser Tyr Pro Gly Val Glu His Val Gly Gly Asp Met
240                 245                 250 ttt gtt agt gtt cca aaa gga gat gcc att ttc atg aag tgg ata tgt      876
Phe Val Ser Val Pro Lys Gly Asp Ala Ile Phe Met Lys Trp Ile Cys
255                 260                 265                 270 cat gat tgg agc gat gaa cac tgc ttg aag ttt ttg aag aaa tgt tat      924
His Asp Trp Ser Asp Glu His Cys Leu Lys Phe Leu Lys Lys Cys Tyr
            275                 280                 285 gaa gca ctt cca acc aat ggg aag gtg atc ctt gct gaa tgc atc ctc      972
Glu Ala Leu Pro Thr Asn Gly Lys Val Ile Leu Ala Glu Cys Ile Leu
        290                 295                 300 ccc gtg gcg cca gac gca agc ctc ccc act aag gca gtg gtc cat att     1020
Pro Val Ala Pro Asp Ala Ser Leu Pro Thr Lys Ala Val Val His Ile
305                 310                 315 gat gtc atc atg ttg gct cat aac cca ggt ggg aaa gag aga act gag     1068
Asp Val Ile Met Leu Ala His Asn Pro Gly Gly Lys Glu Arg Thr Glu
320                 325                 330 aag gag ttt gag gcc ttg gcc aag ggg gct gga ttt gaa ggt ttc cga     1116
Lys Glu Phe Glu Ala Leu Ala Lys Gly Ala Gly Phe Glu Gly Phe Arg
335                 340                 345                 350 gta gta gcc tcg tgc gct tac aat aca tgg atc atc gaa ttt ttg aag     1164
Val Val Ala Ser Cys Ala Tyr Asn Thr Trp Ile Ile Glu Phe Leu Lys
            355                 360                 365 aag att tgagtcctta ctcggctttg agtacataat accaactcct tttggttttc     1220
Lys Ile
gagattgtga ttgtgattgt gattgtctct ctttcgcagt tggccttatg atataatgta     1280
tcgttaactc gatcacagaa gtgcaaaaga cagtgaatgt acactgcttt ataaaataaa     1340 aatttttaaga ttttgattca tgtaaaaaaa aaaaaaaaaa                          1380

<210> SEQ ID NO 6
<211> LENGTH: 368
<212> TYPE: PRT
<213> ORGANISM: Liquidambar styraciflua

<400> SEQUENCE: 6

Met Gly Ser Thr Ser Glu Thr Lys Met Ser Pro Ser Glu Ala Ala Ala
 1               5                  10                  15

Ala Glu Glu Glu Ala Phe Val Phe Ala Met Gln Leu Thr Ser Ala Ser
            20                  25                  30

Val Leu Pro Met Val Leu Lys Ser Ala Ile Glu Leu Asp Val Leu Glu
        35                  40                  45

Ile Met Ala Lys Ala Gly Pro Gly Ala His Ile Ser Thr Ser Asp Ile
    50                  55                  60

Ala Ser Lys Leu Pro Thr Lys Asn Pro Asp Ala Ala Val Met Leu Asp
65                  70                  75                  80

Arg Met Leu Arg Leu Leu Ala Ser Tyr Ser Val Leu Thr Cys Ser Leu
                85                  90                  95

Arg Thr Leu Pro Asp Gly Lys Ile Glu Arg Leu Tyr Gly Leu Ala Pro
```

```
                   100                 105                 110
Val Cys Lys Phe Leu Thr Arg Asn Asp Asp Gly Val Ser Ile Ala Ala
            115                 120                 125

Leu Ser Leu Met Asn Gln Asp Lys Val Leu Met Glu Ser Trp Tyr His
    130                 135                 140

Leu Thr Glu Ala Val Leu Glu Gly Gly Ile Pro Phe Asn Lys Ala Tyr
145                 150                 155                 160

Gly Met Thr Ala Phe Glu Tyr His Gly Thr Asp Pro Arg Phe Asn Thr
                165                 170                 175

Val Phe Asn Asn Gly Met Ser Asn His Ser Thr Ile Thr Met Lys Lys
            180                 185                 190

Ile Leu Glu Thr Tyr Lys Gly Phe Glu Gly Leu Gly Ser Val Val Asp
        195                 200                 205

Val Gly Gly Gly Thr Gly Ala His Leu Asn Met Ile Ile Ala Lys Tyr
    210                 215                 220

Pro Met Ile Lys Gly Ile Asn Phe Asp Leu Pro His Val Ile Glu Glu
225                 230                 235                 240

Ala Pro Ser Tyr Pro Gly Val Glu His Val Gly Gly Asp Met Phe Val
                245                 250                 255

Ser Val Pro Lys Gly Asp Ala Ile Phe Met Lys Trp Ile Cys His Asp
            260                 265                 270

Trp Ser Asp Glu His Cys Leu Lys Phe Leu Lys Lys Cys Tyr Glu Ala
        275                 280                 285

Leu Pro Thr Asn Gly Lys Val Ile Leu Ala Glu Cys Ile Leu Pro Val
    290                 295                 300

Ala Pro Asp Ala Ser Leu Pro Thr Lys Ala Val Val His Ile Asp Val
305                 310                 315                 320

Ile Met Leu Ala His Asn Pro Gly Gly Lys Glu Arg Thr Glu Lys Glu
                325                 330                 335

Phe Glu Ala Leu Ala Lys Gly Ala Gly Phe Glu Gly Phe Arg Val Val
            340                 345                 350

Ala Ser Cys Ala Tyr Asn Thr Trp Ile Ile Glu Phe Leu Lys Lys Ile
        355                 360                 365

<210> SEQ ID NO 7
<211> LENGTH: 2025
<212> TYPE: DNA
<213> ORGANISM: Liquidambar styraciflua
<220> FEATURE:
<221> NAME/KEY: CDS
<222> LOCATION: (60)..(1679)

<400> SEQUENCE: 7
cggcacgagc tcattttcca cttctggttt gatctctgca attcttccat cagtcccta          59 atg gag acc caa aca aaa caa gaa gaa atc ata tat cgg tcg aaa ctc         107
Met Glu Thr Gln Thr Lys Gln Glu Glu Ile Ile Tyr Arg Ser Lys Leu
  1               5                  10                  15 ccc gat atc tac atc ccc aaa cac ctc cct tta cat tcg tat tgt ttc         155
Pro Asp Ile Tyr Ile Pro Lys His Leu Pro Leu His Ser Tyr Cys Phe
             20                  25                  30 gag aac atc tca cag ttc ggc tcc cgc ccc tgt ctg atc aat ggc gca         203
Glu Asn Ile Ser Gln Phe Gly Ser Arg Pro Cys Leu Ile Asn Gly Ala
         35                  40                  45 acg ggc aag tat tac aca tat gct gag gtt gag ctc att gcg cgc aag         251
Thr Gly Lys Tyr Tyr Thr Tyr Ala Glu Val Glu Leu Ile Ala Arg Lys
     50                  55                  60
```

```
gtc gca tcc ggc ctc aac aaa ctc ggc gtt cga caa ggt gac atc atc        299
Val Ala Ser Gly Leu Asn Lys Leu Gly Val Arg Gln Gly Asp Ile Ile
 65              70                  75                  80 atg ctt ttg cta ccc aac tcg ccg gag ttc gtg ttt tca att ctc ggc        347
Met Leu Leu Leu Pro Asn Ser Pro Glu Phe Val Phe Ser Ile Leu Gly
                85                  90                  95 gca tcc tac cgc ggg gct gcc gcc acc gcc gca aac ccg ttt tat acc        395
Ala Ser Tyr Arg Gly Ala Ala Ala Thr Ala Ala Asn Pro Phe Tyr Thr
            100                 105                 110 cct gcc gag atc agg aag caa gcc aaa acc tcc aac gcc agg ctt att        443
Pro Ala Glu Ile Arg Lys Gln Ala Lys Thr Ser Asn Ala Arg Leu Ile
        115                 120                 125 atc aca cat gcc tgt tac tat gag aaa gtg aag gac ttg gtg gaa gag        491
Ile Thr His Ala Cys Tyr Tyr Glu Lys Val Lys Asp Leu Val Glu Glu
    130                 135                 140 aac gtt gcc aag atc ata tgt ata gac tca ccc ccg gac ggt tgt ttg        539
Asn Val Ala Lys Ile Ile Cys Ile Asp Ser Pro Pro Asp Gly Cys Leu
145                 150                 155                 160 cac ttc tcg gag ctg agt gag gcg gac gag aac gac atg ccc aat gta        587
His Phe Ser Glu Leu Ser Glu Ala Asp Glu Asn Asp Met Pro Asn Val
                165                 170                 175 gag att gac ccc gat gat gtg gtg gcg ctg ccg tac tcg tca ggg acg        635
Glu Ile Asp Pro Asp Asp Val Val Ala Leu Pro Tyr Ser Ser Gly Thr
            180                 185                 190 acg ggt tta cca aag ggg gtg atg cta aca cac aag gga caa gtg acg        683
Thr Gly Leu Pro Lys Gly Val Met Leu Thr His Lys Gly Gln Val Thr
        195                 200                 205 agt gtg gcg caa cag gtg gac gga gag aat ccg aac ctg tat ata cat        731
Ser Val Ala Gln Gln Val Asp Gly Glu Asn Pro Asn Leu Tyr Ile His
    210                 215                 220 agc gag gac gtg gtt ctg tgc gtg ttg cct ctg ttt cac atc tac tcg        779
Ser Glu Asp Val Val Leu Cys Val Leu Pro Leu Phe His Ile Tyr Ser
225                 230                 235                 240 atg aac gtc atg ttt tgc ggg tta cga gtt ggt gcg gcg att ctg att        827
Met Asn Val Met Phe Cys Gly Leu Arg Val Gly Ala Ala Ile Leu Ile
                245                 250                 255 atg cag aaa ttt gaa ata tat ggg ttg tta gag ctg gtc aga agt aca        875
Met Gln Lys Phe Glu Ile Tyr Gly Leu Leu Glu Leu Val Arg Ser Thr
            260                 265                 270 ggt gac cat cat gcc tat cgt aca ccc atc gta ttg gca atc tcc aag        923
Gly Asp His His Ala Tyr Arg Thr Pro Ile Val Leu Ala Ile Ser Lys
        275                 280                 285 act ccg gat ctt cac aac tat gat gtg tcc tcc att cgg act gtc atg        971
Thr Pro Asp Leu His Asn Tyr Asp Val Ser Ser Ile Arg Thr Val Met
    290                 295                 300 tca ggt gcg gct cct ctg ggc aag gaa ctt gaa gat tct gtc aga gct       1019
Ser Gly Ala Ala Pro Leu Gly Lys Glu Leu Glu Asp Ser Val Arg Ala
305                 310                 315                 320 aag ttt ccc acc gcc aaa ctt ggt cag gga tat gga atg acg gag gca       1067
Lys Phe Pro Thr Ala Lys Leu Gly Gln Gly Tyr Gly Met Thr Glu Ala
                325                 330                 335 ggg ccc gtg cta gcg atg tgt ttg gca ttt gcc aag gaa ggg ttt gaa       1115
Gly Pro Val Leu Ala Met Cys Leu Ala Phe Ala Lys Glu Gly Phe Glu
            340                 345                 350 ata aaa tcg ggg gca tct gga act gtt tta agg aac gca cag atg aag       1163
Ile Lys Ser Gly Ala Ser Gly Thr Val Leu Arg Asn Ala Gln Met Lys
        355                 360                 365 att gtg gac cct gaa acc ggt gtc act ctc cct cga aac caa ccc gga       1211
Ile Val Asp Pro Glu Thr Gly Val Thr Leu Pro Arg Asn Gln Pro Gly
    370                 375                 380
```

```
gag att tgc att aga gga gac caa atc atg aaa ggt tat ctt aat gat    1259
Glu Ile Cys Ile Arg Gly Asp Gln Ile Met Lys Gly Tyr Leu Asn Asp
385                 390                 395                 400 cct gag gcg acg gag aga acc ata gac aag gaa ggt tgg tta cac aca    1307
Pro Glu Ala Thr Glu Arg Thr Ile Asp Lys Glu Gly Trp Leu His Thr
                405                 410                 415 ggt gat gtg ggc tac atc gac gat gac act gag ctc ttc att gtt gat    1355
Gly Asp Val Gly Tyr Ile Asp Asp Asp Thr Glu Leu Phe Ile Val Asp
            420                 425                 430 cgg ttg aag gaa ctg atc aaa tac aaa ggg ttt cag gtg gca ccc gct    1403
Arg Leu Lys Glu Leu Ile Lys Tyr Lys Gly Phe Gln Val Ala Pro Ala
        435                 440                 445 gag ctt gag gcc atg ctc ctc aac cat ccc aac atc tct gat gct gcc    1451
Glu Leu Glu Ala Met Leu Leu Asn His Pro Asn Ile Ser Asp Ala Ala
    450                 455                 460 gtc gtc cca atg aaa gac gat gaa gct gga gag ctc cct gtg gcg ttt    1499
Val Val Pro Met Lys Asp Asp Glu Ala Gly Glu Leu Pro Val Ala Phe
465                 470                 475                 480 gtt gta aga tca gat ggt tct cag ata tcc gag gct gaa atc agg caa    1547
Val Val Arg Ser Asp Gly Ser Gln Ile Ser Glu Ala Glu Ile Arg Gln
                485                 490                 495 tac atc gca aaa cag gtg gtt ttt tat aaa aga ata cat cgc gta ttt    1595
Tyr Ile Ala Lys Gln Val Val Phe Tyr Lys Arg Ile His Arg Val Phe
            500                 505                 510 ttc gtc gaa gcc att cct aaa gcg ccc tct ggc aaa atc ttg cgg aag    1643
Phe Val Glu Ala Ile Pro Lys Ala Pro Ser Gly Lys Ile Leu Arg Lys
        515                 520                 525 gac ctg aga gcc aaa ttg gcg tct ggt ctt ccc aat taattctcat         1689
Asp Leu Arg Ala Lys Leu Ala Ser Gly Leu Pro Asn
    530                 535                 540 tcgctaccct cctttctctt atcatacgcc aacacgaacg aagaggctca attaaacgct    1749
gctcattcga agcggctcaa ttaaagctgc tcattcatgt ccaccgagtg ggcagcctgt    1809
cttgttggga tgttctttca tttgattcag ctgtgagaag ccagaccctc attatttatt    1869
gtgaaattca caagaatgtc tgtaaatcga tgttgtgagt gatgggtttc aaaacacttt    1929
tgacattgtt tacgttgtat ttcctgctgt tgaaaataac tactttgtat gacttttatt    1989
tgggaagata acctttcaaa aaaaaaaaaa aaaaaa                              2025

<210> SEQ ID NO 8
<211> LENGTH: 540
<212> TYPE: PRT
<213> ORGANISM: Liquidambar styraciflua

<400> SEQUENCE: 8

Met Glu Thr Gln Thr Lys Gln Glu Glu Ile Ile Tyr Arg Ser Lys Leu
 1               5                  10                  15

Pro Asp Ile Tyr Ile Pro Lys His Leu Pro Leu His Ser Tyr Cys Phe
            20                  25                  30

Glu Asn Ile Ser Gln Phe Gly Ser Arg Pro Cys Leu Ile Asn Gly Ala
        35                  40                  45

Thr Gly Lys Tyr Tyr Thr Tyr Ala Glu Val Glu Leu Ile Ala Arg Lys
    50                  55                  60

Val Ala Ser Gly Leu Asn Lys Leu Gly Val Arg Gln Gly Asp Ile Ile
65                  70                  75                  80

Met Leu Leu Leu Pro Asn Ser Pro Glu Phe Val Phe Ser Ile Leu Gly
                85                  90                  95
```

-continued

```
Ala Ser Tyr Arg Gly Ala Ala Thr Ala Ala Asn Pro Phe Tyr Thr
            100                 105                 110
Pro Ala Glu Ile Arg Lys Gln Ala Lys Thr Ser Asn Ala Arg Leu Ile
            115                 120                 125
Ile Thr His Ala Cys Tyr Tyr Glu Lys Val Lys Asp Leu Val Glu Glu
            130                 135                 140
Asn Val Ala Lys Ile Ile Cys Ile Asp Ser Pro Pro Asp Gly Cys Leu
145                 150                 155                 160
His Phe Ser Glu Leu Ser Glu Ala Asp Glu Asn Asp Met Pro Asn Val
                    165                 170                 175
Glu Ile Asp Pro Asp Asp Val Val Ala Leu Pro Tyr Ser Ser Gly Thr
                    180                 185                 190
Thr Gly Leu Pro Lys Gly Val Met Leu Thr His Lys Gly Gln Val Thr
            195                 200                 205
Ser Val Ala Gln Gln Val Asp Gly Glu Asn Pro Asn Leu Tyr Ile His
            210                 215                 220
Ser Glu Asp Val Val Leu Cys Val Leu Pro Leu Phe His Ile Tyr Ser
225                 230                 235                 240
Met Asn Val Met Phe Cys Gly Leu Arg Val Gly Ala Ala Ile Leu Ile
                    245                 250                 255
Met Gln Lys Phe Glu Ile Tyr Gly Leu Leu Glu Leu Val Arg Ser Thr
            260                 265                 270
Gly Asp His His Ala Tyr Arg Thr Pro Ile Val Leu Ala Ile Ser Lys
            275                 280                 285
Thr Pro Asp Leu His Asn Tyr Asp Val Ser Ser Ile Arg Thr Val Met
            290                 295                 300
Ser Gly Ala Ala Pro Leu Gly Lys Glu Leu Glu Asp Ser Val Arg Ala
305                 310                 315                 320
Lys Phe Pro Thr Ala Lys Leu Gly Gln Gly Tyr Gly Met Thr Glu Ala
                    325                 330                 335
Gly Pro Val Leu Ala Met Cys Leu Ala Phe Ala Lys Glu Gly Phe Glu
            340                 345                 350
Ile Lys Ser Gly Ala Ser Gly Thr Val Leu Arg Asn Ala Gln Met Lys
            355                 360                 365
Ile Val Asp Pro Glu Thr Gly Val Thr Leu Pro Arg Asn Gln Pro Gly
            370                 375                 380
Glu Ile Cys Ile Arg Gly Asp Gln Ile Met Lys Gly Tyr Leu Asn Asp
385                 390                 395                 400
Pro Glu Ala Thr Glu Arg Thr Ile Asp Lys Glu Gly Trp Leu His Thr
                    405                 410                 415
Gly Asp Val Gly Tyr Ile Asp Asp Thr Glu Leu Phe Ile Val Asp
                    420                 425                 430
Arg Leu Lys Glu Leu Ile Lys Tyr Lys Gly Phe Gln Val Ala Pro Ala
            435                 440                 445
Glu Leu Glu Ala Met Leu Leu Asn His Pro Asn Ile Ser Asp Ala Ala
            450                 455                 460
Val Val Pro Met Lys Asp Asp Glu Ala Gly Glu Leu Pro Val Ala Phe
465                 470                 475                 480
Val Val Arg Ser Asp Gly Ser Gln Ile Ser Glu Ala Glu Ile Arg Gln
                    485                 490                 495
Tyr Ile Ala Lys Gln Val Val Phe Tyr Lys Arg Ile His Arg Val Phe
            500                 505                 510
Phe Val Glu Ala Ile Pro Lys Ala Pro Ser Gly Lys Ile Leu Arg Lys
```

```
                515                 520                 525
Asp Leu Arg Ala Lys Leu Ala Ser Gly Leu Pro Asn
    530                 535                 540
```

<210> SEQ ID NO 9
<211> LENGTH: 1544
<212> TYPE: DNA
<213> ORGANISM: Pinus taeda

<400> SEQUENCE: 9

```
aaagataata tatgtgtatg cctactacta cacattgttt tgaagtgtgt aaacatagtg      60
caacactagg aggactcaca atgagcactt gttgacatga aactagctaa atgcccaaca    120
atattagtga aagctagtta aactaacccc tttgactttc aagatgatat atttatatcc    180
ctactacgtc ttcctctttt tgtctttctc ttgtgattaa accttccttg aaacaattct    240
caaatgtaaa attaaacctt gaacttgta gagaccaaac ttccctagga gaaaccacat     300
ttatgacaac atatatacac caacccattg catactataa tattggaatt acctgcagcg    360
aacgaaagaa acgctgtctc accaactcgt gcactacatc ccgaaactta accttcccct    420
gatacagatt gaagagccga aaaagcgtg catccaaatt tctggtatgg tgaggagccg      480
aaaaacgcgt gcgcctaatt tttttgagat gggccggaaa ataatgcgtg catctaaatt    540
ttcacgtgtc gcgtattggc gaggttgcgc tgaatgtgat cctgtgcgtg agccacattc    600
attccattgg ttgacccgcc ggtaccgcga ggaccgtggg gtctcacaga tacgcggatg    660
gtggatcagc actgagaaga ttagatgatg accaggcggg catttgaagt aaaaacttgg    720
gggtggttgg caagtacgcg acaagagggg gtagtgcgca aggaagcgag ttggatgcaa    780
ataatattac aaagtgggtt ggtgggcatg agcatcaacc agaatgatgt tgttgctggt    840
tccgtgcaaa ttctgaccag tagtttgaac aatactaccc aacttgtttt tggtaaaaca    900
tgaagtgggt aaggagaatt gaacttacgt ctcatggtaa agggcaaggg caaatgactt    960
aacacatacc tttaactaat aaaaataccc ctaacaaata cgaaaacgaa tgagttatca   1020
cagaccttca actaataaga tagccatcag acccacatct cctgactgac caaaaacaaa   1080
tgacttcaac caactaagat acccatcaaa gctaacccac aacccaattc ctcacttccc   1140
cttaccagac caaccaagca gacctacgcc attaactact ttaggacgtg ggaattgggg   1200
gtgccaccgt tgaagaatgg cactcagggt tggtaatccc tccacgtgta tgtagcagtc   1260
gtttggtgga gacggcgtgt tgaatgtcc accttccagt ttggagaaca aggaaattgg     1320
gcttatatta ggcctggatc tcttgtttca gagcaggagt agttcaggac aggaactagc    1380
attcaagaat tcaattgccc tgccctgctc tgctctgctt tgctcaactt attgatccct    1440
gctctggttt gttcaatttc ttgacccctg ctgggttctg ctctggtttg cacactttct    1500
cgattatata agtcattttg gatccttgca aggaagagaa tatg                    1544
```

<210> SEQ ID NO 10
<211> LENGTH: 659
<212> TYPE: DNA
<213> ORGANISM: Pinus taeda

<400> SEQUENCE: 10

```
aaacaccaat ttaatgggat ttcagatttg tatcccatgc tattggctaa ggcattttc      60
ttattgtaat ctaaccaatt ctaatttcca ccctggtgtg aactgactga caaatgcggt    120
ccgaaaacag cgaatgaaat gtctgggtga tcggtcaaac aagcggtggg cgagagagcg    180
```

```
cgggtgttgg cctagccggg atggggtag gtagacggcg tattaccggc gagttgtccg      240
aatggagttt tcggggtagg tagtaacgta gacgtcaatg gaaaaagtca taatctccgt      300
caaaaatcca accgctcctt cacatcgcag agttggtggc cacggaccc tccacccact      360 cactcaatcg atcgcctgcc gtggttgccc attattcaac catacgccac ttgactcttc      420
accaacaatt ccaggccggc tttctataca atgtactgca caggaaaatc caatataaaa      480
agccggcctc tgcttccttc tcagtagccc ccagctcatt caattcttcc cactgcaggc      540
tacatttgtc agacacgttt tccgccattt ttcgcctgtt tctgcggaga atttgatcag      600
gttcggattg ggattgaatc aattgaaagg ttttttatttt cagtatttcg atcgccatg      659

<210> SEQ ID NO 11
<211> LENGTH: 2251
<212> TYPE: DNA
<213> ORGANISM: Pinus taeda

<400> SEQUENCE: 11
ggccgggtgg tgacatttat tcataaattc atctcaaaac aagaaggatt tacaaaaata      60
aaagaaaaca aaattttcat ctttaacata attataattg tgttcacaaa attcaaactt     120
aaacccttaa tataaagaat ttctttcaac aatacacttt aatcacaact tcttcaatca     180
caacctcctc caacaaaatt aaaatagatt aataaataaa taaacttaac tatttaaaaa     240
aaaatattat acaaaattta ttaaaacttc aaaataaaca aactttttat acaaaattca     300
tcaaaacttt aaaataaagc taaacactga aaatgtgagt acatttaaaa ggacgctgat     360
cacaaaaatt ttgaaaacat aaacaaactt gaaactctac cttttaagaa tgagtttgtc     420
gtctcattaa ctcattagtt ttatagttcg aatccaatta acgtatcttt tatttatgg     480 ataagggtg ttttaataag tgatttggg atttttttag taatttattt gtgatatgtt     540
atggagtttt taaaaatata tatatatata tatatttttg ggttgagttt acttaaaatt     600
tggaaaaggt tggtaagaac tataaattga gttgtgaatg agtgttttat ggattttta     660 agatgttaaa tttatatatg taattaaaat tttattttga ataacaaaaa ttataattgg     720
ataaaaaatt gttttgttaa atttagagta aaaatttcaa atctaaaat aattaaacac     780 tattattttt aaaaaatttg ttggtaaatt ttatcttata tttaagttaa aatttagaaa     840
aaattaattt taaattaata aacttttgaa gtcaaatatt ccaaatattt tccaaaatat     900
taaatctatt ttgcattcaa aatacaattt aaataataaa acttcatgga atagattaac     960
caatttgtat aaaaaccaaa aatctcaaat aaaatttaaa ttacaaaaca ttatcaacat    1020
tatgatttca agaaagacaa taaccagttt ccaataaaat aaaaaacctc atggcccgta    1080
attaagatct cattaattaa ttcttatttt ttaattttt tacatagaaa atatctttat    1140
attgtatcca agaaatatag aatgttctcg tccagggact attaatctcc aaacaagttt    1200
caaaatcatt acattaaagc tcatcatgtc atttgtggat tggaaattat attgtataag    1260
agaaatatag aatgttctcg tctagggact attaatttcc aaacaaattt caaaatcatt    1320
acattaaagc tcatcatgtc atttgtggat tggaaattag acaaaaaaaa tcccaaatat    1380
ttctctcaat ctcccaaaat atagttcgaa ctccatattt ttggaaattg agaatttttt    1440
tacccaataa tatattttt tatacatttt agagattttc cagacatatt tgctctggga    1500
tttattggaa tgaaggttga gttataaact ttcagtaatc caagtatctt cggtttttga    1560
agatactaaa tccattatat aataaaaaca cattttaaac accaatttaa tgggatttca    1620
gatttgtatc ccatgctatt ggctaaggca ttttctttat tgtaatctaa ccaattctaa    1680
```

```
tttccaccct ggtgtgaact gactgacaaa tgcggtccga aaacagcgaa tgaaatgtct    1740
gggtgatcgg tcaaacaagc ggtgggcgag agagcgcggg tgttggccta gccgggatgg    1800
gggtaggtag acggcgtatt accggcgagt tgtccgaatg gagttttcgg ggtaggtagt    1860
aacgtagacg tcaatggaaa aagtcataat ctccgtcaaa aatccaaccg ctccttcaca    1920
tcgcagagtt ggtggccacg ggaccctcca cccactcact cgatcgcctg ccgtggttgc    1980
ccattattca accatacgcc acttgactct tcaccaacaa ttccaggccg gctttctata    2040
caatgtactg cacaggaaaa tccaatataa aaagccggcc tctgcttcct ctcagtagc    2100 ccccagctca ttcaattctt cccactgcag gctacatttg tcagacacgt tttccgccat    2160
ttttcgcctg tttctgcgga gaatttgatc aggttcggat tgggattgaa tcaattgaaa    2220
ggtttttatt ttcagtattt cgatcgccat g                                   2251
```

<210> SEQ ID NO 12
<211> LENGTH: 20
<212> TYPE: PRT
<213> ORGANISM: Artificial Sequence
<220> FEATURE:
<223> OTHER INFORMATION: Description of Artificial Sequence: degenerate
      primer #22 used for amplifying OMT fragments

<400> SEQUENCE: 12

Gly Gly Met Ala Thr Tyr Cys Cys Ala Thr Thr Tyr Ala Ala Cys Ala
 1               5                  10                  15

Ala Gly Gly Cys
            20

<210> SEQ ID NO 13
<211> LENGTH: 20
<212> TYPE: PRT
<213> ORGANISM: Artificial Sequence
<220> FEATURE:
<223> OTHER INFORMATION: Description of Artificial Sequence:degenerate
      primer #23 used for amplifying OMT fragments

<400> SEQUENCE: 13

Ala Ala Ala Gly Ala Gly Ala Gly Asn Ala Cys Asn Asn Ala Asn Asn
 1               5                  10                  15

Ala Asn Gly Ala
            20

<210> SEQ ID NO 14
<211> LENGTH: 31
<212> TYPE: PRT
<213> ORGANISM: Artificial Sequence
<220> FEATURE:
<223> OTHER INFORMATION: Description of Artificial Sequence:primer "R1S"
      used to amplify CCL fragments

<400> SEQUENCE: 14

Thr Thr Gly Gly Ala Thr Cys Cys Gly Gly Ile Ala Cys Ile Ala Cys
 1               5                  10                  15

Ile Gly Gly Ile Tyr Thr Ile Cys Cys Ile Ala Ala Arg Gly Gly
            20                  25                  30

<210> SEQ ID NO 15
<211> LENGTH: 31
<212> TYPE: PRT
<213> ORGANISM: Artificial Sequence
<220> FEATURE:
<223> OTHER INFORMATION: Description of Artificial Sequence: primer "H1S" used for amplifying CCL fragments

<400> SEQUENCE: 15

Thr Thr Gly Gly Ala Thr Cys Cys Gly Thr Ile Gly Thr Ile Gly Cys
 1               5                  10                  15

Ile Cys Ala Arg Cys Ala Arg Gly Thr Ile Gly Ala Tyr Gly Gly
            20                  25                  30

<210> SEQ ID NO 16
<211> LENGTH: 27
<212> TYPE: PRT
<213> ORGANISM: Artificial Sequence
<220> FEATURE:
<223> OTHER INFORMATION: Description of Artificial Sequence: primer
      "R2A" used for amplifying CCL fragments

<400> SEQUENCE: 16

Cys Cys Ile Cys Thr Tyr Thr Ala Asp Ala Cys Arg Thr Ala Asp Gly
 1               5                  10                  15

Cys Ile Cys Cys Ala Gly Cys Thr Gly Thr Ala
            20                  25

<210> SEQ ID NO 17
<211> LENGTH: 12
<212> TYPE: DNA
<213> ORGANISM: Artificial Sequence
<220> FEATURE:
<223> OTHER INFORMATION: Description of Artificial Sequence: oligo-dT
      primer "T11A"

<400> SEQUENCE: 17
tttttttttt ta                                                      12

<210> SEQ ID NO 18
<211> LENGTH: 12
<212> TYPE: DNA
<213> ORGANISM: Artificial Sequence
<220> FEATURE:
<223> OTHER INFORMATION: Description of Artificial Sequence: oligo-dT
      primer "T11C"

<400> SEQUENCE: 18
tttttttttt tc                                                      12

<210> SEQ ID NO 19
<211> LENGTH: 12
<212> TYPE: DNA
<213> ORGANISM: Artificial Sequence
<220> FEATURE:
<223> OTHER INFORMATION: Description of Artificial Sequence: oligo-dT
      primer "T11G"

<400> SEQUENCE: 19
tttttttttt tg                                                      12

<210> SEQ ID NO 20
<211> LENGTH: 13
<212> TYPE: PRT
<213> ORGANISM: Artificial Sequence
<220> FEATURE:
<223> OTHER INFORMATION: Description of Artificial Sequence: OMT
      gene-specific primer

<400> SEQUENCE: 20

Cys Cys Asn Gly Gly Asn Gly Gly Ser Ala Arg Gly Ala
 1               5                  10

```
<210> SEQ ID NO 21
<211> LENGTH: 7
<212> TYPE: PRT
<213> ORGANISM: Artificial Sequence
<220> FEATURE:
<223> OTHER INFORMATION: Description of Artificial Sequence: highly
      degenerated sense primer used to find putative FA5H cDNA fragments

<400> SEQUENCE: 21

Glu Glu Phe Arg Pro Glu Arg
  1               5

<210> SEQ ID NO 22
<211> LENGTH: 9
<212> TYPE: PRT
<213> ORGANISM: Artificial Sequence
<220> FEATURE:
<223> OTHER INFORMATION: Description of Artificial Sequence:  highly
      conserved region in P450 proteins

<400> SEQUENCE: 22

Phe Gly Xaa Gly Xaa Xaa Cys Xaa Gly
  1               5

<210> SEQ ID NO 23
<211> LENGTH: 26
<212> TYPE: DNA
<213> ORGANISM: Artificial Sequence
<220> FEATURE:
<223> OTHER INFORMATION: Description of Artificial Sequence:
      LsFA5H-im1-S primer

<400> SEQUENCE: 23
atggctttcc ttctaatacc catctc                                              26

<210> SEQ ID NO 24
<211> LENGTH: 26
<212> TYPE: DNA
<213> ORGANISM: Artificial Sequence
<220> FEATURE:
<223> OTHER INFORMATION: Description of Artificial Sequence:
      LsFA5H-im-1-A primer

<400> SEQUENCE: 24
gggtgtaatg gacgagcaag gacttg                                              26
```